United States Patent
Bomstad et al.

(10) Patent No.: US 10,119,225 B2
(45) Date of Patent: *Nov. 6, 2018

(54) SYSTEMS FOR CONTROLLING A MANUFACTURING LINE USED TO CONVERT A PAPER WEB INTO PAPER PRODUCTS BY READING MARKS ON THE PAPER WEB

(71) Applicant: GPCP IP Holdings LLC, Atlanta, GA (US)

(72) Inventors: Andrew G. Bomstad, Green Bay, WI (US); Thomas J. Petersen, Green Bay, WI (US); Joseph A. Schulz, Appleton, WI (US); Gregory T. Johnson, Kelso, WA (US); Mark F. Gerrits, De Pere, WI (US)

(73) Assignee: GPCP IP Holdings LLC, Atlanta, GA (US)

( * ) Notice: Subject to any disclaimer, the term of this patent is extended or adjusted under 35 U.S.C. 154(b) by 485 days.

This patent is subject to a terminal disclaimer.

(21) Appl. No.: 14/685,967

(22) Filed: Apr. 14, 2015

(65) Prior Publication Data
US 2015/0292163 A1 Oct. 15, 2015

Related U.S. Application Data

(60) Provisional application No. 61/980,022, filed on Apr. 15, 2014.

(51) Int. Cl.
*D21G 9/00* (2006.01)
*D21H 19/68* (2006.01)
(Continued)

(52) U.S. Cl.
CPC ............ *D21G 9/0009* (2013.01); *D21F 11/14* (2013.01); *D21G 9/0027* (2013.01);
(Continued)

(58) Field of Classification Search
CPC ............ B65H 2220/01; B65H 2220/02; B65H 2511/24; B65H 2511/512; B65H 2553/42;
(Continued)

(56) References Cited

U.S. PATENT DOCUMENTS

| 4,134,684 A | 1/1979 | Jette |
| 4,315,794 A | 2/1982 | Palmieri |

(Continued)

FOREIGN PATENT DOCUMENTS

WO 2013/096397 A1 6/2013

OTHER PUBLICATIONS

International Preliminary Report on Patentability dated Oct. 27, 2016, in corresponding International Patent Application No. PCT/US2015/025915.

(Continued)

*Primary Examiner* — Jose A Fortuna
(74) *Attorney, Agent, or Firm* — Laura L. Bozek

(57) ABSTRACT

A system for producing a paper product. The system includes a paper machine, an analysis tool, and a converting line. The paper machine forms a paper web having a plurality of sections, inspects the paper web to identify web properties, and marks the paper web with a plurality of marks. The analysis tool assigns action scores to each section of the paper web based upon the identified properties that section of the paper web. The converting line reads at least one of the plurality of marks on the paper web, obtains the action score associated with a second one of the plurality of marks, calculates a distance between the at least one mark read by the reading unit and the second one of the plurality of marks, and changes at least one operational parameter of the converting line when the calculated distance is less than a threshold.

58 Claims, 33 Drawing Sheets

(51) Int. Cl.
*D21H 25/00* (2006.01)
*D21F 9/00* (2006.01)
*G01N 21/89* (2006.01)
*G01N 27/61* (2006.01)
*D21H 19/72* (2006.01)
*D21H 27/00* (2006.01)
*D21F 11/14* (2006.01)

(52) U.S. Cl.
CPC ........... *D21G 9/0045* (2013.01); *D21H 19/68* (2013.01); *D21H 19/72* (2013.01); *D21H 25/005* (2013.01); *D21H 27/005* (2013.01); *G01N 21/89* (2013.01); *G01N 27/61* (2013.01); *B05D 2203/22* (2013.01)

(58) Field of Classification Search
CPC .......... B65H 23/1886; B65H 2511/172; B65H 2511/40; B65H 2511/516; B65H 2515/31; B65H 39/16; B65H 2515/314; B65H 2553/822; B65H 2557/242; B65H 2551/20; B65H 2701/124; D21H 25/005; D21H 19/68; D21H 19/72; D21H 27/005; D21F 11/14; D21F 9/00; D21G 9/0045; D21G 9/0036; D21G 9/0009; D21G 9/0027; D06H 3/08; G01N 21/89; G01N 21/8915; G01N 21/8901; G01N 27/61; G01N 33/48764; G01N 35/00732
See application file for complete search history.

(56) References Cited

U.S. PATENT DOCUMENTS

| | | | |
|---|---|---|---|
| 4,534,253 A | 8/1985 | Seragnoli | |
| 4,700,627 A | 10/1987 | Hagler | |
| 4,951,223 A | 8/1990 | Wales et al. | |
| 5,415,123 A | 5/1995 | Ryder | |
| 5,458,062 A | 10/1995 | Goldberg et al. | |
| 5,483,893 A | 1/1996 | Isaac et al. | |
| 5,628,574 A | 5/1997 | Crowley | |
| 5,774,177 A | 6/1998 | Lane | |
| 5,839,688 A | 11/1998 | Hertel et al. | |
| 5,854,683 A | 12/1998 | Keane | |
| 6,174,586 B1 | 1/2001 | Peterson | |
| 6,259,109 B1 | 7/2001 | Dalmia et al. | |
| 6,264,420 B1 | 7/2001 | Bieringer et al. | |
| 6,264,533 B1 | 7/2001 | Kummeth et al. | |
| 6,273,313 B1 | 8/2001 | Noll et al. | |
| 6,299,730 B1 | 10/2001 | Broek et al. | |
| 6,452,679 B1 | 9/2002 | Workman, Jr. | |
| 6,661,507 B2 | 12/2003 | Yoda et al. | |
| 6,699,360 B2 | 3/2004 | Heath et al. | |
| 6,709,549 B2 | 3/2004 | Berglund et al. | |
| 6,725,123 B1 | 4/2004 | Denuell | |
| 6,934,028 B2 | 8/2005 | Ho et al. | |
| 7,027,934 B2 | 4/2006 | Skeps et al. | |
| 7,120,515 B2 | 10/2006 | Floeder et al. | |
| 7,123,981 B2 | 10/2006 | Dollevoet et al. | |
| 7,130,710 B2 | 10/2006 | Popp et al. | |
| 7,187,995 B2 | 3/2007 | Floeder et al. | |
| 7,297,969 B1 | 11/2007 | Wolinsky et al. | |
| 7,384,505 B2 | 6/2008 | Zoller et al. | |
| 7,542,821 B2 | 6/2009 | Floeder et al. | |
| 7,780,817 B2 | 8/2010 | Hellstrom | |
| 7,797,133 B2 | 9/2010 | Floeder et al. | |
| 7,937,233 B2 | 5/2011 | Floeder et al. | |
| 7,957,000 B2 | 6/2011 | Hofeldt et al. | |
| 7,967,407 B2 | 6/2011 | Moscato et al. | |
| 7,974,459 B2 | 7/2011 | Floeder et al. | |
| 8,023,720 B2 | 9/2011 | Reunanen et al. | |
| 8,060,234 B2 | 11/2011 | Hellstrom et al. | |
| 8,080,130 B2 | 12/2011 | Harper et al. | |
| 8,157,199 B2 | 4/2012 | Sartain et al. | |
| 8,168,254 B2 | 5/2012 | Dovertie et al. | |
| 8,175,739 B2 | 5/2012 | Floeder et al. | |
| 8,195,323 B2 | 6/2012 | Simone | |
| 8,238,646 B2 | 8/2012 | Floeder et al. | |
| 8,453,959 B2 | 6/2013 | Sartain et al. | |
| 8,545,574 B2 | 10/2013 | Vinson et al. | |
| 8,820,238 B2 | 9/2014 | Brandenburg et al. | |
| 8,931,411 B2 | 1/2015 | Schnabel et al. | |
| 8,935,104 B2 | 1/2015 | Floeder et al. | |
| 9,142,023 B2 | 9/2015 | Floeder et al. | |
| 9,172,916 B2 | 10/2015 | Tarn et al. | |
| 9,284,147 B2 | 3/2016 | Techlin | |
| 9,518,362 B2* | 12/2016 | Bomstad | D21F 11/14 |
| 9,771,686 B2 | 9/2017 | Bomstad et al. | |
| 9,845,574 B2 | 12/2017 | Bomstad et al. | |
| 9,963,827 B2 | 5/2018 | Bomstad et al. | |
| 9,975,720 B2 | 5/2018 | Techlin | |
| 2002/0139499 A1 | 10/2002 | Berglund et al. | |
| 2003/0192662 A1 | 10/2003 | Heath et al. | |
| 2004/0030431 A1 | 2/2004 | Popp et al. | |
| 2004/0083018 A1 | 4/2004 | Dollevoet et al. | |
| 2004/0255396 A1 | 12/2004 | Vinson et al. | |
| 2005/0153100 A1 | 7/2005 | Zoller et al. | |
| 2006/0090319 A1 | 5/2006 | Howe | |
| 2006/0191426 A1 | 8/2006 | Timmerman et al. | |
| 2006/0254367 A1 | 11/2006 | Hellstrom | |
| 2006/0279624 A1 | 12/2006 | Tsuchiya et al. | |
| 2007/0045461 A1 | 3/2007 | Sartain et al. | |
| 2007/0222805 A1 | 9/2007 | Moscato et al. | |
| 2008/0210396 A1 | 9/2008 | Hellstrom | |
| 2009/0030544 A1 | 1/2009 | Floeder et al. | |
| 2009/0048702 A1 | 2/2009 | Simone | |
| 2009/0176008 A1 | 7/2009 | Dovertie et al. | |
| 2009/0194244 A1 | 8/2009 | Harper et al. | |
| 2009/0283601 A1 | 11/2009 | Schultze et al. | |
| 2011/0137451 A1 | 6/2011 | Schultze et al. | |
| 2011/0224918 A1 | 9/2011 | Floeder et al. | |
| 2012/0037742 A1 | 2/2012 | Michal, III et al. | |
| 2012/0147177 A1 | 6/2012 | Tam | |
| 2012/0193464 A1 | 8/2012 | Sartain et al. | |
| 2013/0167744 A1 | 7/2013 | Schnabel et al. | |
| 2014/0084102 A1 | 3/2014 | Techliin | |
| 2014/0096368 A1 | 4/2014 | Roper et al. | |
| 2015/0115976 A1 | 4/2015 | Adams et al. | |
| 2015/0292155 A1* | 10/2015 | Bomstad | D21F 11/14 700/125 |
| 2015/0292156 A1* | 10/2015 | Bomstad | D21F 11/14 162/118 |
| 2015/0292161 A1* | 10/2015 | Bomstad | D21F 11/14 428/199 |
| 2015/0292162 A1* | 10/2015 | Bomstad | D21F 11/14 700/125 |
| 2015/0292163 A1* | 10/2015 | Bomstad | D21F 11/14 700/125 |
| 2016/0362839 A1* | 12/2016 | Bomstad | D21F 11/14 |
| 2018/0058007 A1 | 3/2018 | Bomstad et al. | |

OTHER PUBLICATIONS

Notification of and International Search Report and Written Opinion completed Aug. 17, 2015, and dated Sep. 1, 2015, in corresponding International Patent Application No. PCT/US2015/025915.
2012/0147177 A1, issued as U.S. Pat. No. 9,172,916 B2.
2015/0292156 A1, issued as U.S. Pat. No. 9,518,362 B2.

* cited by examiner

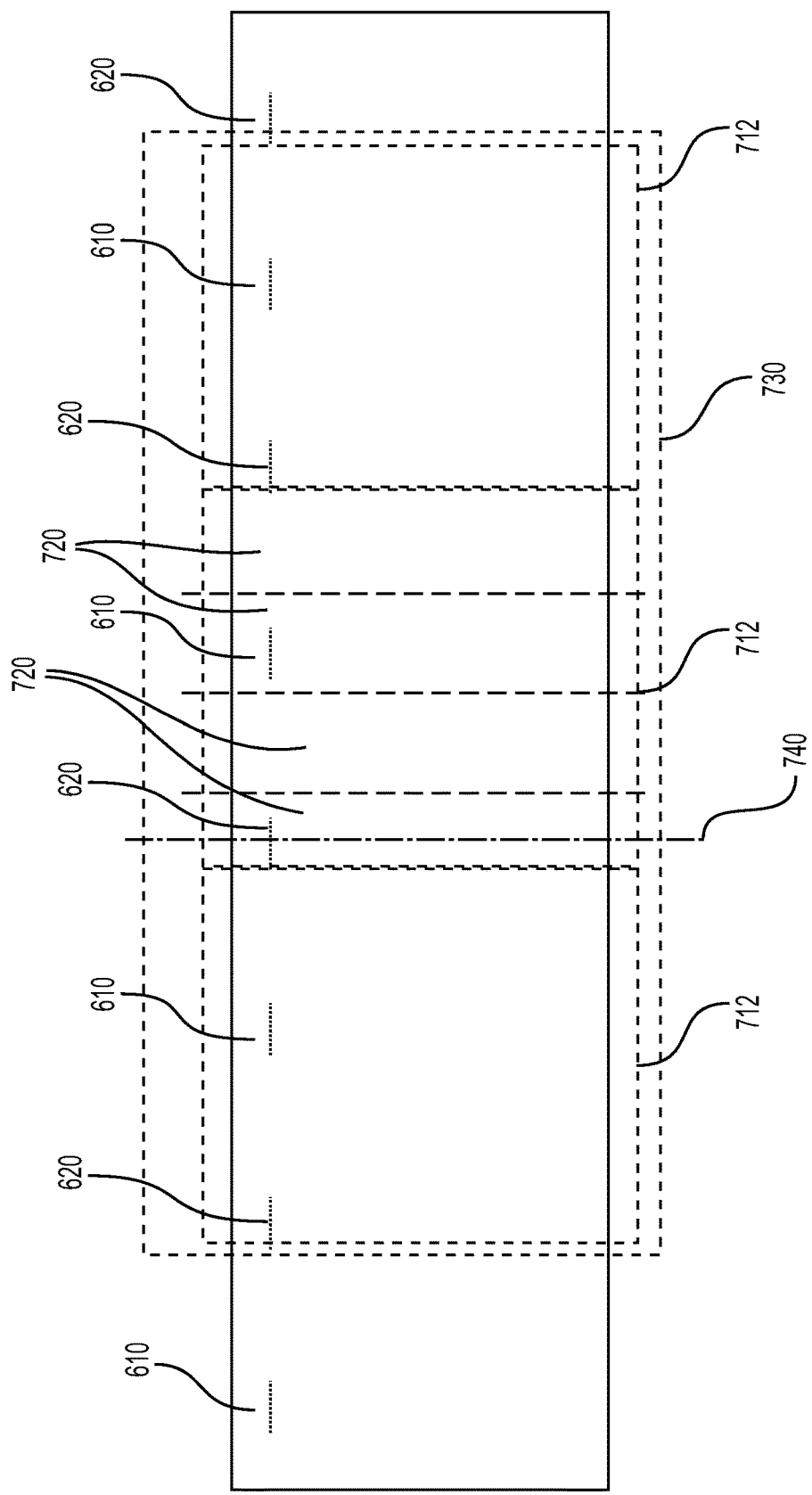

RAW DATA WITH NO ACTION SCORING UPDATE

| DATA TABLE ENTRY | MARK | MARK FOOTAGE | ROLL ID | BREAK | BREAK FOOTAGE | DEFECT AREA | DEFECT ASPECT RATIO | DEFECT MD LOCATION | DEFECT CD LOCATION | WEB BASIS WT | ACTION | ACTION FOOTAGE |
|---|---|---|---|---|---|---|---|---|---|---|---|---|
| 1 | 1 | 200 | 20101 | 0 | 0 | 0 | 0 | 0 | 0 | 16 | 0 | 0 |
| 2 |   | 0 | 20101 | 0 | 0 | 2 | 2 | 390 | 40 | 16 | 0 | 0 |
| 3 |   | 0 | 20101 | 0 | 0 | 2 | 2 | 400 | 50 | 16 | 0 | 0 |
| 4 |   | 0 | 20101 | 0 | 0 | 2 | 2 | 410 | 43 | 16 | 0 | 0 |
| 5 |   | 0 | 20101 | 0 | 0 | 2 | 2 | 420 | 52 | 16 | 0 | 0 |
| 6 |   | 0 | 20101 | 0 | 0 | 2 | 2 | 435 | 38 | 16 | 0 | 0 |
| 7 |   | 0 | 20101 | 0 | 0 | 2 | 2 | 445 | 47 | 16 | 0 | 0 |
| 8 | 2 | 600 | 20101 | 0 | 0 | 0 | 0 | 0 | 0 | 16 | 0 | 0 |
| 9 | 3 | 1000 | 20101 | 0 | 0 | 0 | 0 | 0 | 0 | 16 | 0 | 0 |
| 10 |   |   | 20101 | 0 | 0 | 4 | 2 | 1080 | 97 | 16 | 0 | 0 |
| 11 | 4 | 1400 | 20101 | 0 | 0 | 0 | 0 | 0 | 0 | 16 | 0 | 0 |
| 12 |   |   | 20101 | 0 | 0 | 18 | 2 | 1675 | 80 | 16 | 0 | 0 |
| 13 | 5 | 1800 | 20101 | 0 | 0 | 0 | 0 | 0 | 0 | 16 | 0 | 0 |
| 14 |   |   | 20101 | 1 | 2175 | 0 | 0 | 0 | 0 | 16 | 0 | 0 |
| 15 | 6 | 2400 | 20101 | 0 | 0 | 0 | 0 | 0 | 0 | 12 | 0 | 0 |
| 16 | 7 | 2800 | 20101 | 0 | 0 | 6 | 2 | 3150 | 85 | 14 | 0 | 0 |
| 17 |   |   | 20101 | 0 | 0 | 0 | 0 | 0 | 0 | 14 | 0 | 0 |
| 18 | 8 | 3200 | 20101 | 0 | 0 | 0 | 0 | 0 | 0 | 14 | 0 | 0 |

*FIG. 9L*

ACTION SCORE AND FOOTAGE UPDATED FOR EACH ANALYSIS

| DATA TABLE ENTRY | MARK | MARK FOOTAGE | ROLL ID | BREAK | BREAK FOOTAGE | DEFECT AREA | DEFECT ASPECT RATIO | DEFECT MD LOCATION | DEFECT CD LOCATION | WEB BASIS WT | ACTION | ACTION FOOTAGE |
|---|---|---|---|---|---|---|---|---|---|---|---|---|
| 1 | 1 | 200 | 20101 | 0 | 0 | 2 | 2 | 0 | 0 | 16 | 0 | 0 |
| 2 |  | 0 | 20101 | 0 | 0 | 2 | 2 | 390 | 40 | 16 | 1 | 600 |
| 3 |  | 0 | 20101 | 0 | 0 | 2 | 2 | 400 | 50 | 16 | 1 | 600 |
| 4 |  | 0 | 20101 | 0 | 0 | 2 | 2 | 410 | 43 | 16 | 1 | 600 |
| 5 |  | 0 | 20101 | 0 | 0 | 2 | 2 | 420 | 52 | 16 | 1 | 600 |
| 6 |  | 0 | 20101 | 0 | 0 | 2 | 2 | 435 | 38 | 16 | 1 | 600 |
| 7 |  | 0 | 20101 | 0 | 0 | 2 | 2 | 445 | 47 | 16 | 1 | 600 |
| 8 | 2 | 600 | 20101 | 0 | 0 | 0 | 0 | 0 | 0 | 16 | 0 | 0 |
| 9 | 3 | 1000 | 20101 | 0 | 0 | 0 | 0 | 0 | 0 | 16 | 0 | 0 |
| 10 |  | 0 | 20101 | 0 | 0 | 4 | 2 | 1080 | 97 | 16 | 1 | 1400 |
| 11 | 4 | 1400 | 20101 | 0 | 0 | 0 | 0 | 0 | 0 | 16 | 0 | 0 |
| 12 |  | 0 | 20101 | 0 | 0 | 18 | 2 | 1675 | 80 | 16 | 1 | 1800 |
| 13 | 5 | 1800 | 20101 | 0 | 0 | 0 | 0 | 0 | 0 | 16 | 0 | 0 |
| 14 |  | 0 | 20101 | 1 | 2175 | 0 | 0 | 0 | 0 | 16 | 1 | 2400 |
| 15 | 6 | 2400 | 20101 | 0 | 0 | 0 | 0 | 0 | 0 | 16 | 1 | 2800 |
| 16 | 7 | 2800 | 20101 | 0 | 0 | 0 | 0 | 0 | 0 | 12 | 0 | 0 |
| 17 |  | 0 | 20101 | 0 | 0 | 6 | 2 | 3150 | 85 | 14 | 1 | 3200 |
| 18 | 8 | 3200 | 20101 | 0 | 0 | 0 | 0 | 0 | 0 | 14 | 0 | 0 |

*FIG. 9M*

ACTION SCORE AND FOOTAGE PUSHED THROUGH TABLE

| DATA TABLE ENTRY | MARK | MARK FOOTAGE | ROLL ID | BREAK | BREAK FOOTAGE | DEFECT AREA | DEFECT ASPECT RATIO | DEFECT MD LOCATION | DEFECT CD LOCATION | WEB BASIS WT | ACTION | ACTION FOOTAGE |
|---|---|---|---|---|---|---|---|---|---|---|---|---|
| 1 | 1 | 200 | 20101 | 0 | 0 | 2 | 2 | 0 | 0 | 16 | 0 | 0 |
| 2 |   | 0 | 20101 | 0 | 0 | 2 | 2 | 390 | 40 | 16 | 1 | 600 |
| 3 |   | 0 | 20101 | 0 | 0 | 2 | 2 | 400 | 50 | 16 | 1 | 600 |
| 4 |   | 0 | 20101 | 0 | 0 | 2 | 2 | 410 | 43 | 16 | 1 | 600 |
| 5 |   | 0 | 20101 | 0 | 0 | 2 | 2 | 420 | 52 | 16 | 1 | 600 |
| 6 |   | 0 | 20101 | 0 | 0 | 2 | 2 | 435 | 38 | 16 | 1 | 600 |
| 7 |   | 0 | 20101 | 0 | 0 | 2 | 2 | 445 | 47 | 16 | 1 | 600 |
| 8 | 2 | 600 | 20101 | 0 | 0 | 0 | 0 | 0 | 0 | 16 | 1 | 600 |
| 9 | 3 | 1000 | 20101 | 0 | 0 | 4 | 2 | 1080 | 97 | 16 | 1 | 1400 |
| 10 |   |   | 20101 | 0 | 0 | 0 | 0 | 0 | 0 | 16 | 1 | 1400 |
| 11 | 4 | 1400 | 20101 | 0 | 0 | 18 | 2 | 1675 | 80 | 16 | 1 | 1800 |
| 12 |   |   | 20101 | 0 | 0 | 0 | 0 | 0 | 0 | 16 | 1 | 1800 |
| 13 | 5 | 1800 | 20101 | 1 | 2175 | 0 | 0 | 0 | 0 | 16 | 1 | 2400 |
| 14 |   |   | 20101 | 0 | 0 | 0 | 0 | 0 | 0 | 16 | 1 | 2400 |
| 15 | 6 | 2400 | 20101 | 0 | 0 | 6 | 2 | 3150 | 85 | 12 | 1 | 2800 |
| 16 | 7 | 2800 | 20101 | 0 | 0 | 0 | 0 | 0 | 0 | 14 | 1 | 3200 |
| 17 |   |   | 20101 | 0 | 0 | 0 | 0 | 0 | 0 | 14 | 1 | 3200 |
| 18 | 8 | 3200 | 20101 | 0 | 0 | 0 | 0 | 0 | 0 | 14 | 1 | 3200 |

*FIG. 9N*

SYSTEMS FOR CONTROLLING A MANUFACTURING LINE USED TO CONVERT A PAPER WEB INTO PAPER PRODUCTS BY READING MARKS ON THE PAPER WEB

CROSS REFERENCE TO RELATED APPLICATION

This application is based on U.S. Provisional Patent Application No. 61/980,022, filed Apr. 15, 2014, which is incorporated herein in its entirety.

FIELD OF THE INVENTION

Our invention relates to methods, systems, and marks for manufacturing paper products such as paper towels and bathroom tissue. In particular, our invention relates to a method of controlling a manufacturing line to convert a paper web into paper products and a converting line implementing this method. Our invention also relates to a mark for a paper web and a method of marking a paper web.

BACKGROUND OF THE INVENTION

In a typical paper manufacturing process, a paper web is created on a paper machine and wound onto a large roll called a parent roll. The paper web is then unwound from the parent roll and converted into consumer sized products on a converting line. In paper manufacturing, as in many manufacturing processes, efficient operations that maximize operational time are desired. Defects may occur, however, in the paper web as it is being manufactured on the paper machine. These defects may be significant enough to cause the paper web to break while, for example, the web is being unwound on the converting line. A web break reduces productivity in the converting line, because an operator must stop the converting line in order to re-thread the paper web. This process may take from about five minutes to about an hour. At typical converting speeds of about two thousand feet per minute, each web break reduces the amount of paper product produced by about ten thousand feet up to about one hundred twenty thousand feet. It is, therefore, desirable to accurately identify these web defects and take action on the converting line to prevent web breaks from occurring.

The inspection of a paper web while it is being created on a paper machine is commonly performed in the art. There are also many patents, such as U.S. Pat. No. 6,452,679, directed towards web inspection. Inspection of the paper web on the paper machine is commonly used to provide real-time feedback for the papermaking process. In this way, the paper machine can be adjusted to minimize the generation of defects or to adjust other parameters of the paper web, such as basis weight.

The defect information from the web inspection may also be used to repair or to remove the portions of the paper web having the defect, before these portions result in a web break on the converting line or a failure during operation. In U.S. Pat. No. 6,934,028, a paper web is inspected, and defects are classified and located relative to periodically placed fiduciary indicators. Using these fiduciary indicators, a portion of the web having a defect may be identified and removed. Similarly, in U.S. Pat. No. 7,297,969, a paper web is inspected, periodically marked, and wound on a reel. This patent discloses a mark sequence in which the spaces between the starting points of adjacent marks are used to encode a location along the length of the web. These marks may then be used to locate defects on the paper web that were identified during inspection. The paper web is placed on a repair machine and the reel is unwound. The marks are used to stop the unwinding at a defect location so that the defect may be repaired. While not using a repair machine, U.S. Pat. No. 6,725,123 likewise discloses using marks to stop a converting line, so that a defect may be repaired. U.S. Pat. No. 8,060,234 discloses a method and an apparatus similar to that discussed in U.S. Pat. No. 6,725,123. But, instead of using marks to subsequently identify a location on a paper web on a converting line, U.S. Pat. No. 8,060,234 discloses using an optical signature for one lane of the paper web. The optical signature is the small-scale and large-scale variability inherent in a paper web.

In another method known in the art, defects are identified during web inspection and located based on their position relative to one end of the paper web. The position of the paper web may be located as a function of the diameter of a parent roll. A laser may then be used to measure the diameter of the parent roll as it is unwound, in order to locate a defect on the paper web. While the laser may be very precise, small out-of-round conditions on the parent roll may have a large impact on the position of the paper web as measured by the laser. Accordingly, this method has a large uncertainty.

In another method, a web defect is marked with a physical tag, such as a tag disclosed in U.S. Pat. No. 5,415,123. This method is heavily reliant on operator skill and expertise, because it requires the operator to observe the tag and to take action to stop the converting line in a sufficient amount of time to prevent the defect from causing a web to break.

A series of patents, for example, U.S. Pat. No. 7,937,233; U.S. Pat. No. 8,175,739; and U.S. Pat. No. 8,238,646, discloses a system in which a paper web is inspected for defects and periodically marked with "fiducial marks." This system then creates a defect map where defects identified during the inspection are mapped relative to the fiducial marks. These defect maps are then used to apply locating marks at the position of the defects. Because the paper web is cut into smaller sections, a converting plan can be created to more effectively utilize the paper by cutting around the defects. Further, the defect maps may be used to sort the paper web into different grades of paper.

Each of these methods treats the defects individually and establishes other individual action points to stop and to repair or to discard a portion of the paper web. There is thus a need for improved methods and systems for defect identification, marking, and converting line control.

SUMMARY OF THE INVENTION

According to one aspect, our invention relates to a system for producing a paper product. The system includes a paper machine for forming a paper web, an analysis tool, and a converting line for converting the paper web into a paper product. The paper web produced by the paper machine has a plurality of sections in a sequence. The paper machine includes a web analysis unit to perform at least one of inspecting the paper web and identifying properties in the paper web. The paper machine also includes a marking unit to mark the paper web with a plurality of marks. At least one mark is assigned to each of the plurality of sections. The paper machine further includes a winder to wind the paper web into a parent roll. The winder is positioned after the web analysis unit and the marking unit. The analysis tool is configured to assign an action score to each section of the paper web based upon the identified properties in that section of the paper web. At least one action score has an action value. The converting line has a plurality of operating parameters. The converting line includes an unwind stand to unwind the paper web from the parent roll. The converting line also includes a mark reading unit that reads at least one of the plurality of marks on the paper web and produces a corresponding output from the mark that has been read. The converting line further includes a controller that is configured to obtain the action score associated with a second one of the plurality of marks, to calculate a distance between the at least one mark read by the reading unit and the second one of the plurality of marks, and to change at least one operational parameter of the converting line based upon the action score of the second one of the plurality of marks when the calculated distance is less than a threshold. The second one of the plurality of marks is the next mark with an action value after the at least one mark read by the reading unit. The converting line yet further includes a finisher. The paper web is fed to the finisher and converted into a paper product.

According to another aspect, our invention relates to a method of producing a paper product. The method includes forming a paper web on a paper machine. The paper web has a plurality of sections in a sequence. The method also includes analyzing the paper web with a web analysis unit to perform at least one of inspecting the paper web and identifying properties in the paper web. The method further includes marking the paper web with a plurality of marks. At least one mark is marked at each of the plurality of sections. The method yet further includes winding the paper web with the winder to form a parent roll after the paper web has been inspected and marked. The method still further includes assigning an action score to each section of the paper web based upon the properties in that section of the paper web that are identified in the analyzing step. At least one action score has an action value. The method also includes unwinding a paper web from a parent roll on a converting line having a plurality of operational parameters, and reading at least one of the plurality of marks with a mark reading unit. The method further includes obtaining the action score associated with a second one of the plurality of marks, calculating a distance between the at least one mark read by the reading unit and the second one of the plurality of marks, and changing at least one operational parameter of the converting line based upon the action score of the second one of the plurality of marks when the calculated distance is less than a threshold. The second one of the plurality of marks is the next mark with an action value after the at least one mark read by the by the reading unit. The method yet further includes converting the paper web into a paper product.

According to a further aspect, our invention relates to a system for producing a paper product. The system includes a paper machine for forming a paper web, an analysis tool, and a converting line for converting the paper web into a paper product. The paper web produced by the paper machine has a plurality of sections. The paper machine includes a web analysis unit to perform at least one of inspecting the paper web and identifying properties in the paper web. The paper machine also includes a marking unit to mark the paper web with a plurality of marks. At least one mark is assigned to each of the plurality of sections. The paper machine further includes a winder to wind the paper web into a parent roll. The winder is positioned after the web analysis unit and the marking unit. The analysis tool is configured to assign a quality score to each section of the paper web based upon the identified properties in that section of the paper web. At least one quality score has an action value. The converting line has a plurality of operating parameters. The converting line includes an unwind stand to unwind the paper web from the parent roll. The converting line also includes a mark reading unit that reads at least one of the plurality of marks on the paper web and produces a corresponding output from the mark that has been read. The converting line further includes a finisher. The paper web is fed to the finisher and converted into a paper product. The converting line yet further includes a controller that receives the output from the mark reading unit and is configured to obtain the quality score associated with the at least one mark read by the reading unit, and to cause the finisher to reject the paper product corresponding to one of the plurality of paper web sections when the quality score of the at least one mark read by the reading unit has an action value.

According to yet another aspect, our invention relates to a method of producing a paper product. The method includes forming a paper web on a paper machine. The paper web has a plurality of sections. The method also includes analyzing the paper web with a web analysis unit to perform at least one of inspecting the paper web and identifying properties in the paper web, and marking the paper web with a plurality of marks. At least one mark is marked at each of the plurality of sections. The method further includes winding the paper web with the winder to form a parent roll after the paper web has been inspected and marked. The method yet further includes assigning a quality score to each section of the paper web based upon the properties in that section of the paper web that are identified in the analyzing step. At least one quality score has an action value. The methods also includes unwinding a paper web from a parent roll on a converting line having a plurality of operational parameters, and reading at least one of the plurality of marks with a mark reading unit. The method further includes obtaining the quality score associated with the at least one mark read by the reading unit, converting the paper web into a paper product, and rejecting the paper product corresponding to one of the plurality of paper web sections when the quality score of the at least one mark read by the reading unit has an action value.

These and other aspects of our invention will become apparent from the following disclosure.

BRIEF DESCRIPTION OF THE DRAWINGS

FIG. 8 shows an example of how the paper web may be analyzed for defects in conjunction with our invention.

FIGS. 9A through 9C and 9F through 9K are flow charts of steps for assigning inputs for the converting line in accordance with a preferred embodiment of our invention, and FIGS. 9D, 9E, and 9L through 9N show the development of the scored database.

DETAILED DESCRIPTION OF THE PREFERRED EMBODIMENTS

Consumer paper products, such as paper towels, bathroom tissue, and the like, are made by first creating a paper web on a paper machine. This paper web is wound onto large rolls called parent rolls. The parent rolls are then moved to a converting line at which the paper web is unwound from the parent roll and converted into consumer paper products. Our invention relates to methods, systems, and marks for controlling the converting line.

The term "paper product," as used herein, encompasses any product incorporating papermaking fibers having cellulose as a major constituent. This would include, for example, products marketed as paper towels, toilet paper, and facial tissues. Papermaking fibers include virgin pulps or recycle (secondary) cellulosic fibers, or fiber mixes comprising cellulosic fibers. Wood fibers include, for example, those obtained from deciduous and coniferous trees, including softwood fibers, such as northern and southern softwood kraft fibers, and hardwood fibers, such as eucalyptus, maple, birch, aspen, or the like. Examples of other fibers suitable for making the products of our invention include nonwood fibers, such as cotton fibers or cotton derivatives, abaca, kenaf, sabai grass, flax, esparto grass, straw, jute hemp, bagasse, milkweed floss fibers, and pineapple leaf fibers. Furnish refers to aqueous compositions including papermaking fibers, and, optionally, wet strength resins, debonders, and the like, for making paper products.

When describing our invention herein, the terms "machine direction" (MD) and "cross machine direction" (CD) will be used in accordance with their well-understood meaning in the art. That is, the MD of a fabric or other structure refers to the direction that the structure moves on a papermaking machine in a papermaking process, while CD refers to a direction crossing the MD of the structure. Similarly, when referencing paper products, the MD of the paper product refers to the direction on the product that the product moved on the papermaking machine in the papermaking process, and the CD of the product refers to the direction crossing the MD of the product.

When describing our invention herein, specific examples of operating conditions for the paper machine and converting line will be used. For example, various speeds will be used when describing paper production on the paper machine or converting on the converting line. Those skilled in the art will recognize that our invention is not limited to the specific examples of the operating conditions, including speed, that are disclosed herein.

Figure 1:
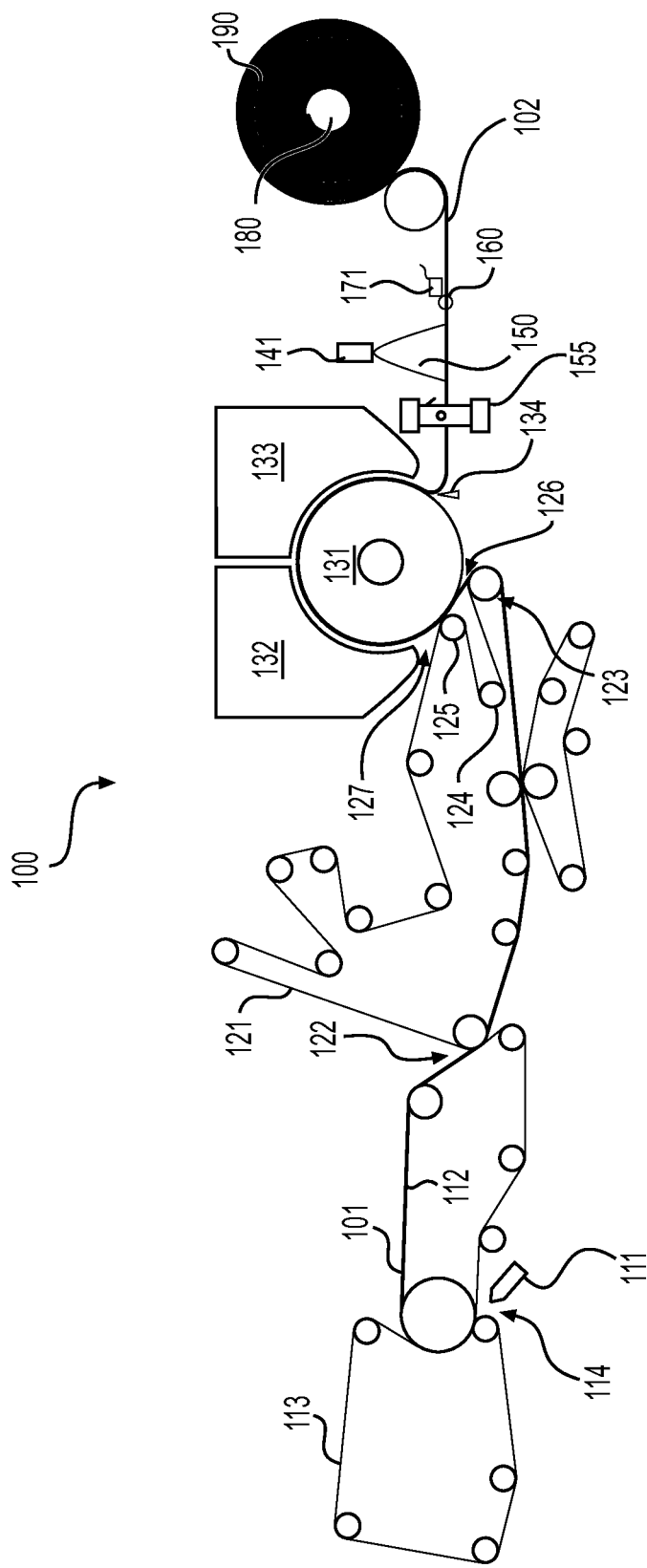
FIG. 1 is a schematic diagram of a papermaking machine configuration that can be used in conjunction with our invention.

Paper webs may be made on a paper machine implementing any one of a number of methods known in the art, such as conventional wet pressing and through-air drying. FIG. 1 is a schematic diagram showing an exemplary twin wire wet crepe machine layout that can readily be adapted to practice our invention. Those skilled in the art will recognize that other paper machines likewise may be readily adapted to practice our invention.

In the paper machine 100 shown in FIG. 1, furnish issues from headbox 111 into nip 114 between inner wire 112 and outer wire 113 to form nascent web 101. The nascent web 101 is carried on the inner wire 112 and transferred to felt 121, at nip 122. The nascent web 101 is then transferred from the felt 121 to Yankee cylinder 131 at nip 126 between suction pressure roll 123 and the Yankee cylinder 131. In this paper machine 100, felt 121 passes over idler roll 124 before passing around blind drilled roll 125 and though nip 127 between the blind drilled roll 125 and the Yankee cylinder 131. The Yankee cylinder 131 is a heated cylinder that is used to dry the nascent web 101. In addition, hot air from wet end hood 132 and dry end hood 133 is directed against the nascent web 101 to further dry the nascent web 101 as it is conveyed on the Yankee cylinder 131. The dried nascent web 101 forms a paper web 102. The paper web 102 is removed from the Yankee cylinder 131 with the help of doctor blade 134. The paper web 102 is then wound around a reel 180 to form a parent roll 190.

Some paper machines create a paper web 102 that is wider than can be used in a subsequent converting process. As a result, the paper web 102 may be split into two or more parent rolls 190 using a cutter 160. The rolls may be designated with a letter such as an A roll or a B roll. The cutter 160 may be a circular blade with a continuous cutting surface. Those skilled in the art will recognize that any suitable cutter may be used including, for example, a water jet cutting system.

Figures 2, 3:
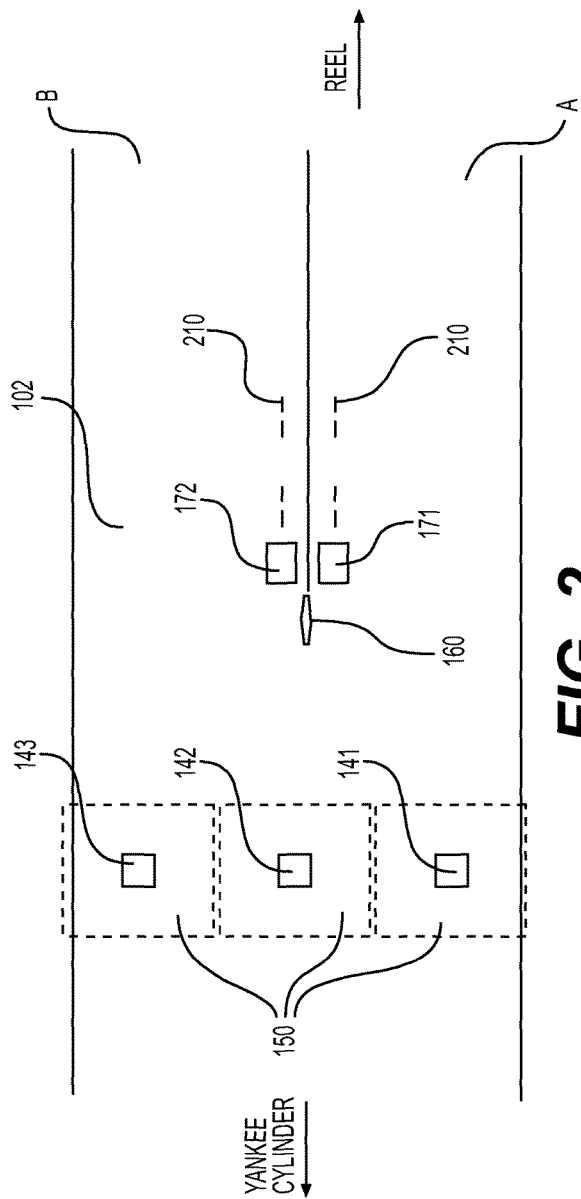
FIG. 2 is a detailed top plan view of the papermaking machine configuration shown in FIG. 1.
FIG. 3 is an exemplary defect database that can be used in conjunction with our invention.

In this preferred embodiment, the paper web 102 is inspected for defects on the paper machine 100. As shown in FIGS. 1 and 2, the paper web 102 is inspected by web inspection units 141, 142, 143 after the paper web 102 leaves the Yankee cylinder 131. The web inspection units are part of a web inspection system. Those skilled in the art will recognize that any suitable web inspection systems and units may be used including those made by ABB of Zurich, Switzerland; Metso of Helsinki, Finland; Papertec of North Vancouver, BC, Canada; Honeywell of Morristown, N.J.; and Event Capture Systems of Mint Hill, N.C. In the preferred embodiment, each web inspection unit 141, 142, 143 includes at least a digital high speed camera and a light source. The cameras of the preferred embodiment are set to take images at, for example, one hundred twenty frames per second and have a resolution of, for example, six hundred forty pixels by four hundred eighty pixels. The web inspection units 141, 142, 143 are positioned a distance above the paper web 102 to preferably have a field of view 150 between about seventy inches and about one hundred four inches wide, and more preferably, about one hundred two inches wide. An example of a suitable camera includes Prosilica GT1910 made by Allied Vision Technologies of Stadtroda, Germany. The web inspection units 141, 142, 143 are also preferably positioned so the entire width of the paper web 102 is inspected. Preferably, the field of view 150 for each web inspection unit 141, 142, 143 has a small amount of overlap of approximately two inches with the field of view 150 of the adjacent web inspection unit 141, 142, 143. The resolution and distance from the paper web determine the size of an indication or a defect that can be detected. Increasing the resolution of the camera will enable smaller defects to be detected. Alternatively, placing the camera closer to the paper web enables smaller defects to be detected, but the field of view is also decreased and more cameras will be needed to image the entire width of the paper web 102. The light source is preferably an array of light emitting diodes used to illuminate the paper web 102. In the preferred embodiment, the light source is positioned coincident with the camera. Those skilled in the art will recognize that any suitable light source may be used, including high frequency florescent lighting or halogen lighting. The light source may also be positioned elsewhere on the paper machine 100 including below the paper web 102. As those skilled in the art will recognize, the lighting requirements will depend upon the camera settings, including frame rate and aperture.

Any suitable web inspection system that is capable of analyzing the captured images to identify and to classify defects may be used. Further, any suitable method of identifying and classifying defects may be used, such as gray scale analysis or image comparison. In the preferred embodiment, defects are identified by using a gray scale method. The paper web 102 appears white to the camera, because the paper web 102 reflects the light from the light source. Defects, on the other hand, are non-reflective and appear dark to the camera. The opposite, where the paper web 102 appears dark to the camera and defects appear white, occurs when the lighting is positioned below the paper web. Defects may thus be identified as pixels in the images captured by web inspection units having a gray scale value darker than a predetermined threshold. Once identified, the dimensions and positions of individual defects may be determined. The defect analysis method discussed in U.S. Patent Appln. Pub. No. 2012/0147177 (the disclosure of which is incorporated by reference in its entirety) may be used to distinguish between true defects and false positives. Many different types of defects may be identified by the web inspection system. In the preferred embodiment, the web inspection units 141, 142, 143 identify holes, tears, wrinkles, chemical coating streaks, and the like.

Figure 4:
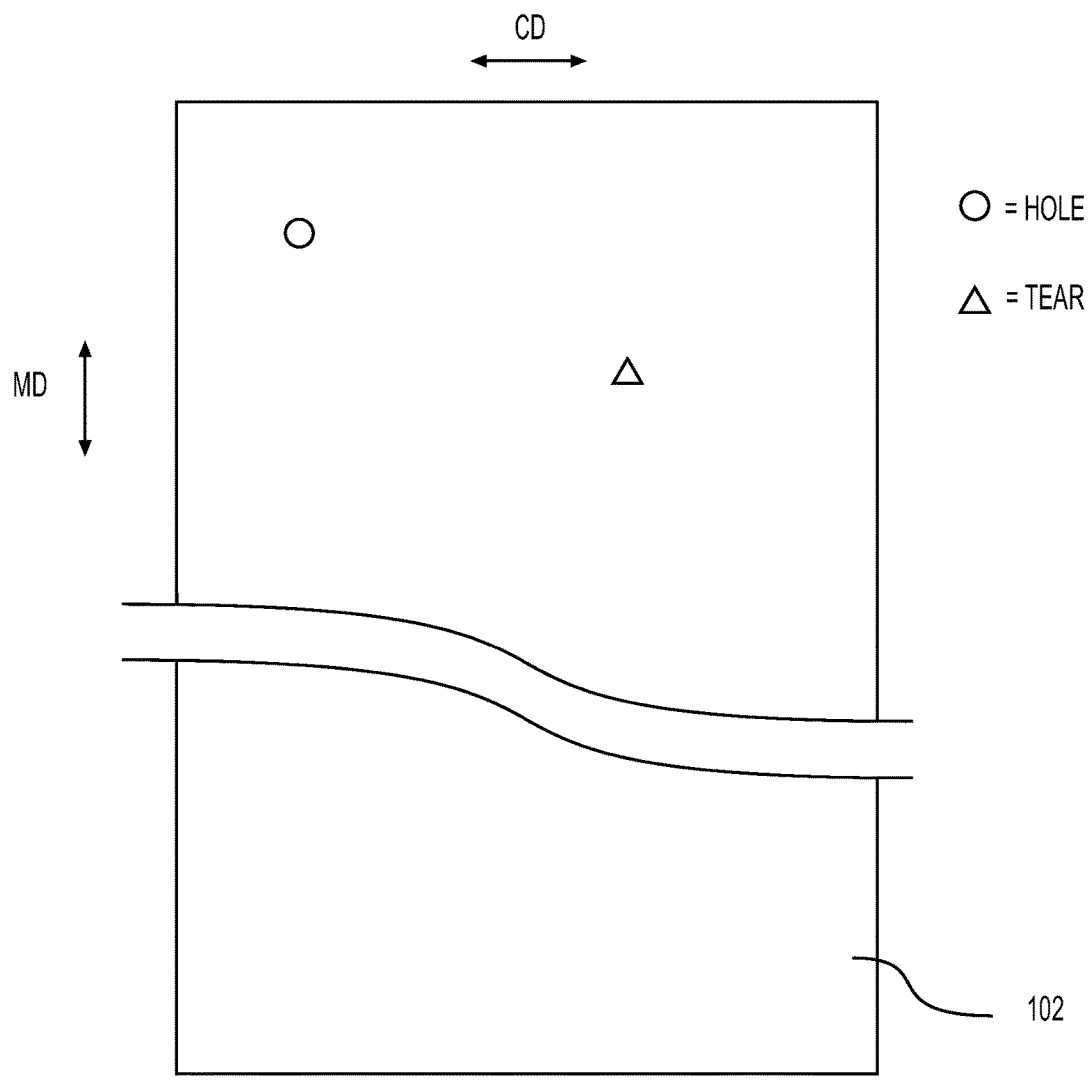
FIG. 4 is a defect map of the defect database shown in FIG. 3.

When the defects are identified by the web inspection system, they are preferably recorded in a table or a database, such as the table shown in FIG. 3. A "database," as used herein, means a collection of data organized in such a way that a computer program may quickly select desired pieces of the data. An example is an electronic filing system. In the preferred embodiment, the time the defect is detected, the location of the defect, and defect specific information are recorded in a database. This database may be referred to as the defect database, and in the preferred embodiment, all data is established in the database with respect to a master time reference. As an example, the leading edge of the paper web 102 in the machine direction passes the web inspection units 141, 142, 143 at 09:34:01. The first web defect is identified at 09:41:10, which is recorded in the defect database. The first defect is located one thousand feet in the machine direction (MD) from the leading edge of the paper web 102 and ten inches from one of the edges of the paper web 102 in the cross-machine direction (CD). By grayscale analysis, the first web defect is identified as having both a length and a width of one half inch, resulting in an aspect ratio of length to width of one. Similarly, the second web defect is recorded at 10:10:00 and has an aspect ratio of 0.0625. Defects may be classified by the aspect ratio. In this case, the first web defect is considered to be a hole and the second web defect is considered to be a tear. This process is then repeated for the entire parent roll. The defects may also be represented graphically in a defect map such as the map shown in FIG. 4. Here, the first web defect is shown with an open circle in the upper left of the paper web 102. The second web defect is similarly shown with an open triangle.

The defect database may be stored in a non-transitory computer-readable medium in order to facilitate the analysis described below. A non-transitory computer readable medium, as used herein, comprises all computer-readable media except for a transitory, propagating signal. Examples of non-transitory computer readable media include, for example, a hard disk drive and/or a removable storage drive, representing a disk drive, a magnetic tape drive, an optical disk drive, etc. The non-transitory computer readable media may be connected to processors, programmable logic controllers for converting line control, the web inspection system using network connections that are common in the art, and other controllers and systems used in our invention. When the non-transitory computer readable media is connected to a network, it may be referred to as a file server.

Other paper web properties may be measured on the paper machine 100, for example, moisture content and basis weight of the paper web. In this embodiment, as shown in FIG. 1, a web property scanner 155 is positioned after the Yankee cylinder 131 and before web inspection units 141, 142, 143. Any suitable web property scanner 155 known in the art may be used to measure web properties. An example of a suitable web property scanner 155 is an MXProLine scanner manufactured by Honeywell of Morristown, N.J., that is used to measure the moisture content with beta radiation and basis weight with gamma radiation. As these data are collected, the web property is recorded in a database along with the time that the property was obtained. This database may be the defect database or a separate database for web properties (e.g., web properties database). In addition, web properties may also be indirectly determined from other operating parameters of the paper machine 100. Operating parameters such as pump speeds, fan speeds, and the like, may be correlated to web properties. By monitoring and recording these operating parameters, web properties can be calculated and recorded in the web properties database.

In order to effectively utilize the defect information generated during web inspection, the paper web 102 is marked at a set periodicity with mark 210. As shown in FIGS. 1 and 2, the paper web 102 is preferably marked after the web inspection units 141, 142, 143 and prior to being wound on the reel 180. In the preferred embodiment, marking units 171, 172 are positioned adjacent to the cutter 160. This position allows for accurate and repeatable application of mark 210. Cutting the paper web 102 requires that the paper web 102 be stable when it is cut, particularly, that the paper web 102 is taut and moved at a constant speed. Both of these conditions are well suited for accurate application of mark 210. Further, the outside edges of the paper web 102 may move in the cross-machine (CD) direction when viewing a particular point on the paper machine 100, because either the width of the paper web 102 changes or the paper web 102 as a whole shifts. By applying mark 210 near the cutter 160, the mark 210 can be positioned at a set distance from an edge of the paper web 102, making reading the mark 210 easier on the converting line and ensuring that the mark 210 is removed when the finished product is cut to length. The MD distance between the web inspection units 141, 142, 143 and the marking units 171, 172 is also preferably minimized. As with the defects, the mark 210 is recorded in the defect database according to a master time reference. Preferably, the same time should correspond to the same MD location on the paper. If the web inspection units 141, 142, 143 and the marking units 171, 172 are separated, however, a correction factor would need to be applied to one of the time references. This introduces a source of uncertainty.

Any suitable marking unit 171, 172 may be used, such as COM-2112 manufactured by Ryeco Inc. of Marietta, Ga. Also, any suitable ink may be used to mark the web, including food grade ink or ink that is visible under ultraviolet light Ink that may be detected under ultraviolet light is advantageous in the event that the mark is not properly removed during the converting process. In this case, the mark is not visible to a consumer, even though the mark remains on the consumer product.

Figure 5:
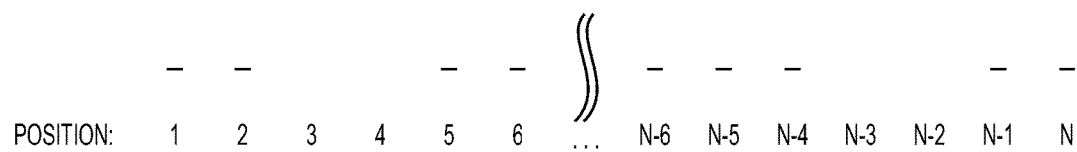
FIG. 5 shows an example of marking that can be used on a paper web in conjunction with our invention.
Figure 6:
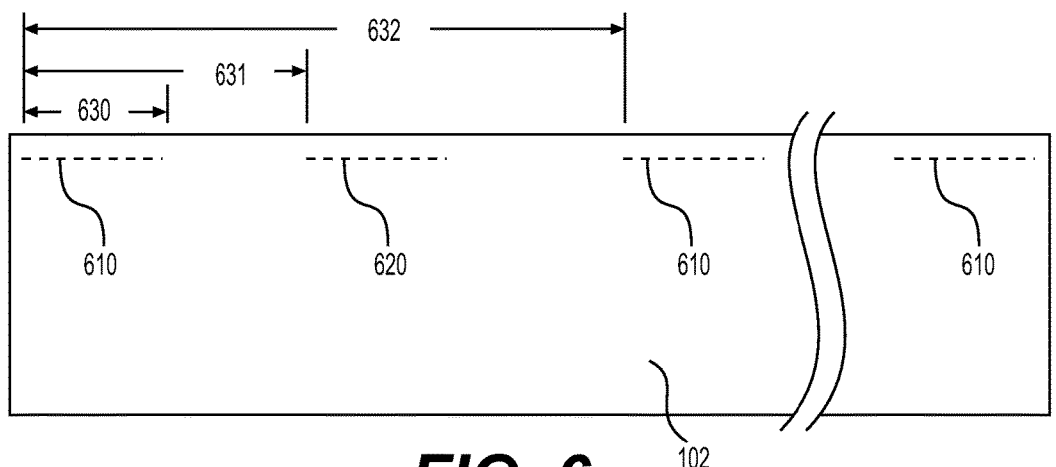
FIG. 6 shows how the marks of FIG. 5 may be applied to a paper web.

The mark of the preferred embodiment is a binary mark made of multiple discrete positions over a set distance of the paper web 102. As shown in FIG. 5, the mark includes N positions. Each position is either blank, indicating a value of zero, or contains ink, indicating a value of one. Ideally, the mark length 630 (see FIG. 6) is as small as possible and could be a bar code. Such a mark could be used to practice our invention, but the marking technology, especially for paper making used for tissue and towel, has not yet advanced to make such marks practical Ink marks have a tendency to spread on the paper web. Thus, it is difficult to precisely control the width of the ink mark as is necessary for a bar code. Additionally, at typical reel speeds of about three thousand five hundred feet per minute, the length of any mark will be limited by the rate of discharge from an ink head. We have thus found that the ink is preferably applied as a dash that is about one thirty-second of an inch in width and about three inches in length. At typical reel speeds, the marking unit 171, 172 discharges ink for about two milliseconds to create a mark of three inches in length. Further, a dash provides a sufficient time for the mark to be detected and read on a converting line. (The converting line speeds may range from about one thousand three hundred feet per minute to about three thousand feet per minute.) A position is preferably less than about twenty inches in length, more preferably, less than about six inches in length, and, most preferably, about three inches in length. The start of each position is similarly preferably separated from adjacent positions by about twenty inches or less, more preferably, about six inches or less, and, most preferably, about three inches. Those skilled in the art will recognize, however, that other types of ink applications, including dots, may be used without deviating from the scope of our invention. The mark preferably contains between about sixteen positions and about sixty-eight positions, and, more preferably, about thirty-eight positions. The number of positions in a mark is a balance between providing enough positions or bits to convey the information contained in the mark and keeping the mark to a reasonable length. A mark as described above with thirty-eight positions will preferably have a mark length 630, as shown in FIG. 6, of about sixteen feet.

In the preferred embodiment, the first two positions (positions one and two in FIG. 5) each contains a dash. Together, the two dashes indicate the start of a mark. Similarly, the last two positions (positions N−1 and N in FIG. 5) will contain a dash to indicate the end of the mark. In reading the mark, a mark reading unit (discussed below) can distinguish between marks when a predetermined amount of time has passed between successive detections of ink. This predetermined amount of time should be longer than the time it takes for the mark to pass by the reading unit.

Figure 7:
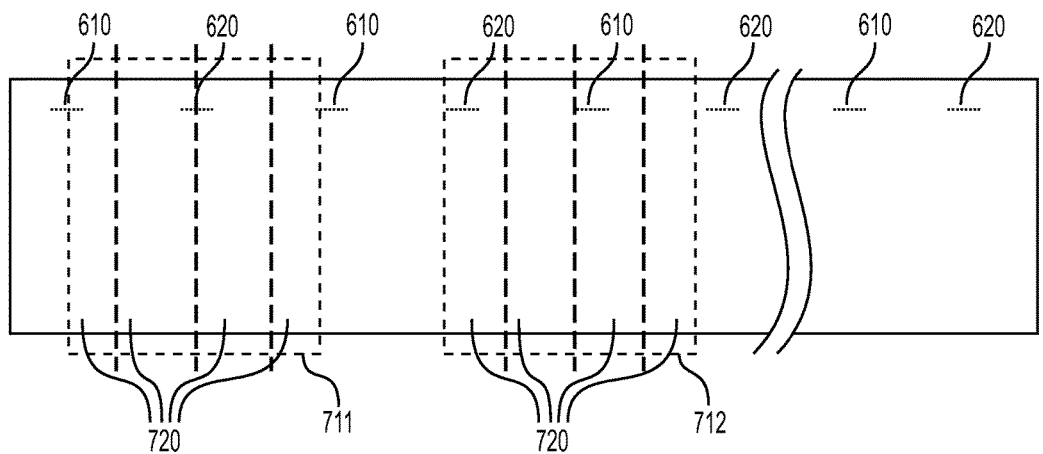
FIG. 7 shows examples of how the paper web may be subdivided.

The remaining thirty-four positions in the preferred embodiment are used to identify the parent roll and the lineal position of the mark on the parent roll. Positions three to five may be used to identify the particular paper machine and the mill from which the roll originated, positions six and seven may be used to identify whether the roll is an A roll or a B roll (as discussed above). Positions eight to twenty-four may be used to identify the specific roll. These positions may also be used to establish an inventory. In the present embodiment, the inventory numbers in positions eight to twenty-four are used on a rotating basis. A number is assigned to a parent roll when it is created. Once the parent roll is converted or otherwise used, the number may then be assigned to another parent roll. Taken together, positions three to twenty-four may be referred to as roll identification information or the parent roll identification number. The remaining positions, twenty-five to thirty-six may be used to convey a particular location with the paper web 102 and may be referred to as location information, linear footage, or MD footage, for example. When these thirty-eight positions are insufficient to convey this information in a single mark, additional positions may be added to the mark. As used hereafter, the foregoing will be referred to as the single mark embodiment where mark 610 and mark 620 shown in FIG. 7 are the same.

Alternatively, two marks can be used. One mark can be a roll identification mark 610 and a second mark can be a location mark 620. Those skilled in the art will recognize that any number of marks may be used to convey the desired information from the paper machine to the converting line. As used hereafter, this type of marking configuration will be referred to as the multi-mark embodiment. In the roll identification mark 610, for example, the positions may be used to identify the particular paper machine and the mill from which the roll originated, used to identify whether the roll is an A roll or a B roll (as discussed above), and used to establish an inventory. In the location mark 620, the positions may be used to convey a particular location within the paper web 102.

In the preferred embodiment shown in FIG. 6, marks 610 and 620 are applied to the paper web 102 at a set periodicity. The marks are spaced such that the distance between the start of adjacent marks 631 is a predetermined distance. In the single mark embodiment, the distance between adjacent marks 631 is the distance of control on the converting line. This distance is thus set as a result of many factors including the speed of the converting line, the ability of the mark reading unit to distinguish between adjacent marks, a goal of minimizing the amount of product recycled, and the like. As will be discussed in more detail below, the distance between adjacent marks 631 may also determine the distance over which the paper web 102 is analyzed to develop converting line control inputs. Closer marks thus result in a finer analysis interval, and a more precise increment for control of the converting line. In addition, more frequent marks reduce the opportunity for error on the converting line. We have found that the distance between adjacent marks 631 is preferably between about two hundred fifty feet and about one thousand feet, and, more preferably, about four hundred feet. In the multi-mark embodiment, successive marks alternate between a roll identification mark 610 and a location mark 620. When two marks are used, the distance between marks of the same type 632 is a predetermined distance. This distance 632 sets the distance of control on the converting line for the multi-mark embodiment. We have found that the distance between marks of the same type 632 is preferably between about three hundred feet and about one thousand feet, and, more preferably, about five hundred feet. We have found that, in the multi-mark embodiment, the distance between adjacent marks 631 is preferably half the distance between marks of the same type 632. In either embodiment, the mark and the time that the mark is applied are recorded in the defect database when a mark 610 or 620 is applied to paper web 102.

Once the defects have been identified and recorded in the defect database, they are then analyzed to develop inputs for converting line control. In the preferred embodiment, this analysis is performed using an analysis tool. Additional information beyond that recorded in the defect database may be useful in establishing converting line control inputs. A consolidated database is thus created by adding this additional information to the defect database. Those skilled in the art will recognize that this additional information includes commonly measured properties of the paper web, such as the moisture content of the paper web, the basis weight of the paper web, the tensile strength of the paper web, and the like. This additional information may include the information stored in the web properties database, discussed above. While the moisture content of the paper web and the basis weight of the paper web may be collected directly on the paper machine 100 (as discussed above), these data may also be collected offline and included in the analysis as an input into the consolidated database. In the following discussion, the moisture content and basis weight will be discussed in the context of collecting these data offline. This additional information may be entered into the consolidated database as a constant value for the entire parent roll or may vary depending upon the location in the parent roll. As with the defect database, if the paper web properties vary along the length of the paper web, the properties are entered using a master time reference. Additionally, other paper web problems, such as a paper web break, may not be automatically included in the defect database from the web inspection system. Locations of web breaks are then input into the consolidated database according to the time of occurrence. In addition, parent rolls 190 may be assigned a so-called "TAPPI Roll Number," which is a number used to identify parent rolls 190 and assigned according to Technical Association of the Pulp and Paper Industry (TAPPI) Technical Information Paper (TIP) 1004-01. The TAPPI Roll Number may also be added to the consolidated database.

Once a consolidated database has been established, the analysis tool then analyzes the consolidated database to develop inputs for converting line control. The objective of the analysis is to generate an output for a specific portion of the web. This portion may be called a block. In the preferred embodiment, each block is associated with the mark containing the linear footage of the parent roll 190 (both marks 610 and 620 in the single mark embodiment and location mark 620 in the multi-mark embodiment). Those skilled in the art will recognize that the paper web 102 may be separated into blocks and associated with a location mark in a number of different ways. As shown in FIG. 7, for example, block 711 may extend from the center of one roll identification mark 610 to the center of the next roll identification mark 610. In this way, block 711 is centered about a location mark 620. Alternatively, block 712 may extend from the beginning of location mark 620 to the beginning of the next location mark 620. Blocks 711, 712 may be further subdivided into segments 720. As shown in FIG. 7, each block 711, 712 is subdivided into four equal segments 720.

Figure 12A:
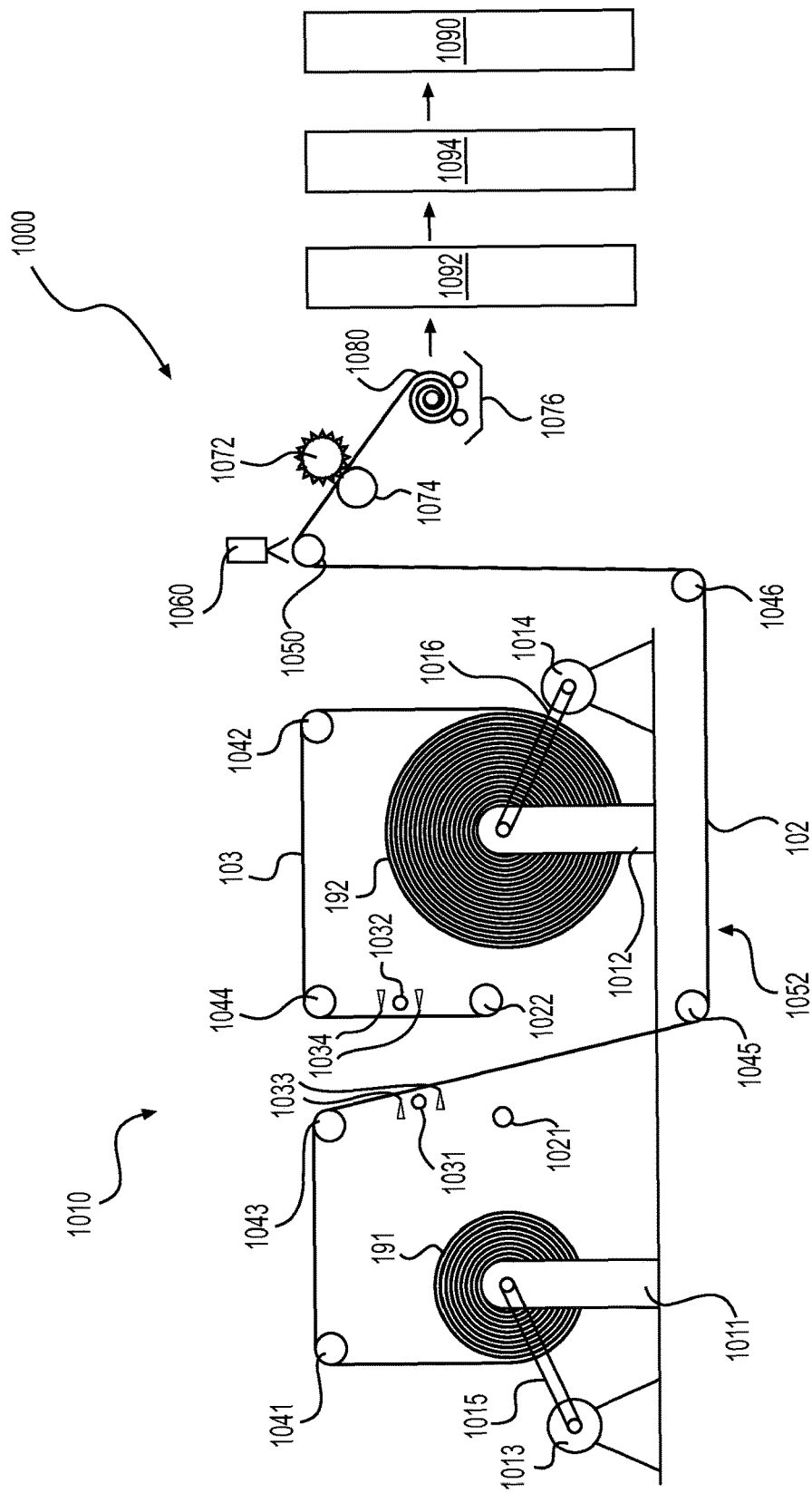
FIGS. 12A and 12B are schematic diagrams of portions of converting line configurations that can be used in conjunction with our invention.

Inputs for converting line control are developed for each block 712 by determining the likelihood of converting line failure for each block 712. Those skilled in the art will recognize that converting line failure refers to a number of different problems that could occur on a converting line. Such problems include the paper web breaking, the paper web wrapping on a roller, and the like. While some web defects and out of specification paper web properties are unlikely to cause converting line failure, these defects or properties may, nonetheless, be undesirable in a consumer product. Such defects or properties are often referred to as quality defects. Inputs for converting line control may also be developed for each block 712 to prevent these quality defects from being converted into consumer products. Any suitable inputs may be used, but we will discuss two approaches. The first approach, used in the preferred embodiment, is to use two criteria, an action score and a quality score, for converting line control. The first criterion is an action score and is established based on the likelihood of converting line failure. The action score may consist of three values: zero, one, or two. An action score of zero indicates a low likelihood of converting line failure. The converting line will not take any action for blocks 712 of the paper web with a score of zero. An action score of one indicates a high likelihood of converting failure with the most appropriate action being not converting that block 712 of the paper web. In this case, the converting line will be stopped to remove the block 712 with an action score of one and/or the converting line will splice to another parent roll 192 (FIG. 12A). An action score of two indicates a moderate likelihood of converting line failure. Here, the block 712 may be converted, but the converting line takes a mitigating action, such as slowing, reducing tension, and the like, to mitigate the risk of converting line failure.

The second criterion is a quality score and is established based on the need to reject a section of the paper web to prevent unacceptable quality defects. The quality score may consist of two values: zero or one. A quality score of zero indicates that there are no identified quality defects in block 712 of the paper web. A quality score of one indicates a quality defect that is unacceptable for delivery to consumers and that block 712 should be removed from further processing. For example, when the converting line is preparing rolled paper product (such as paper towels), a log 1080 (FIG. 12A) may be removed after it is formed and before it is further processed in the log saw 1094 (FIG. 12A).

The second, alternative approach of inputs for converting line control is a fault code and severity level. Fault codes may be, for example, a type of converting line failure or converting line problem, such as break, wrap, quality, and the like. Those skilled in the art will recognize that any number of suitable criteria may be used. The severity level may be a numerical value between, for example, one and ten, with ten being the most severe. A zero value for a severity level may indicate that a fault is unlikely.

The process of assigning the fault code and the severity level or the action score and the quality score will now be described. We have found that with either type of input (fault code and severity level or action score and quality score), a layered or multi-pass analysis approach is preferred. In this approach, the consolidated database is analyzed for one type of defect or defect grouping before moving on to the next defect type. A benefit of the layered or multi-pass analysis approach is that each layer or pass is independent of another. In this way, it is easy to modify the analysis for one particular defect type without the modification impacting the other defect passes. Similarly, it is easy to add or to delete different analysis passes without modifying the other passes. The analyses discussed below may be performed over any suitable analysis window 730, which may include, for example, a single block 712 or multiple blocks 712 as shown in FIG. 8. One having ordinary skill in the art will recognize, however, that our invention is not limited to the following methods of assigning inputs for converting line control. Rather, those skilled in the art will recognize that a number of different approaches may be taken to assign the inputs for converting line control without departing from the scope of our invention.

Figure 9A:
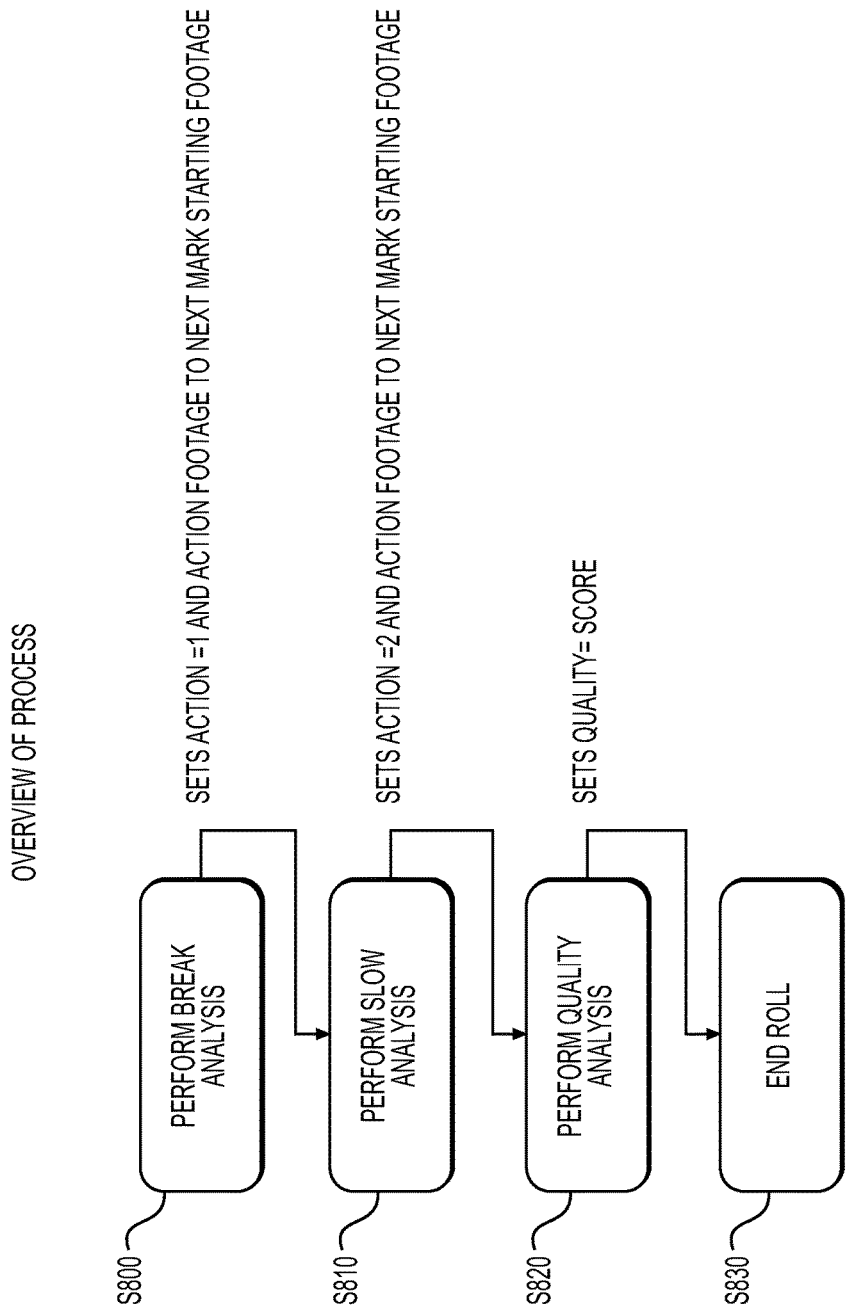

We will now describe the process for assigning an action score and a quality score with reference to FIGS. 9A to 9N and FIGS. 10A and 10B (with periodic reference to FIGS. 1 and 8). The process overview is shown in FIG. 9A. Each block 712 begins the analysis with a default action score and a quality score of zero. In step S800, a break analysis is performed for each block 712 in the parent roll 190. If the analysis determines that a block 712 has a high likelihood of the paper web 102 breaking on the converting line, the action score will be set to one for that block 712 and the action footage will be set to the next mark starting footage (as will be discussed further below). For any blocks 712 in the parent roll 190 not having an action score set to one, a slow analysis is performed in step S810. Here, if the analysis determines that a block 712 has a moderate likelihood of the paper web 102 breaking on the converting line, the action score will be set to two and the action footage will be set to the next mark starting footage. The blocks 712 are then analyzed for quality defects in step S820. If any quality defects are identified, the quality score will be set to one. The analysis is then completed in step S830.

Figure 9B:
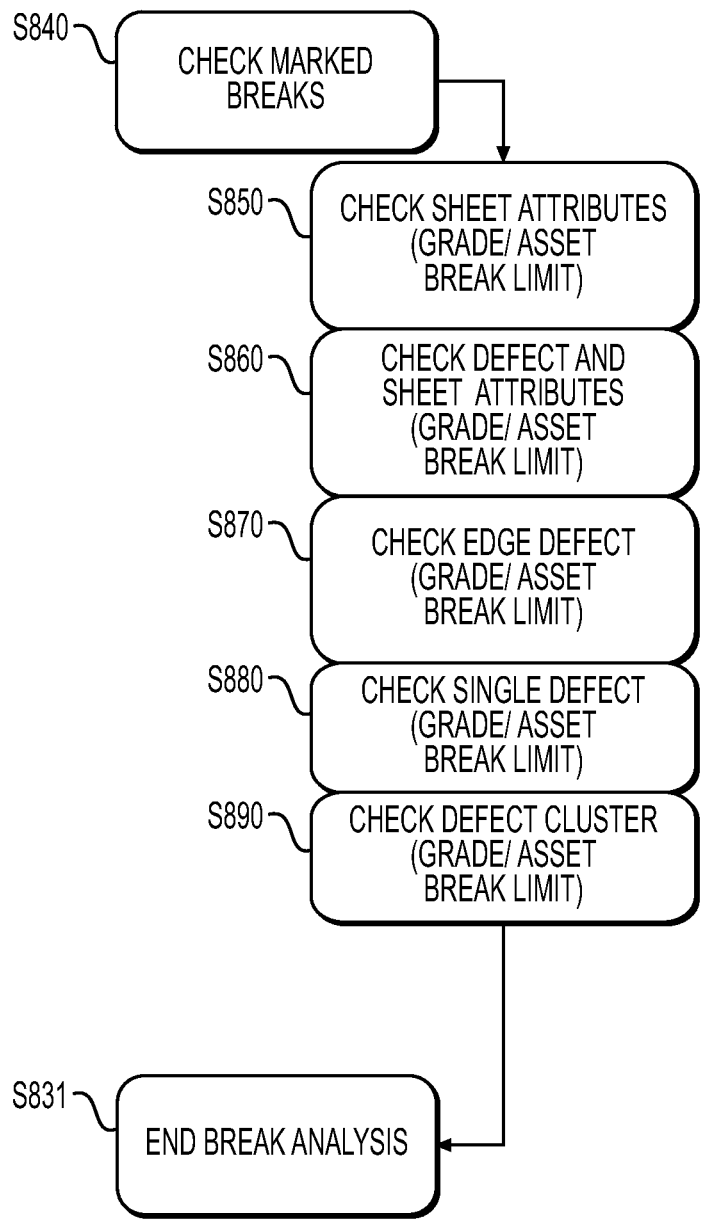

FIG. 9B shows the analyses performed as part of the break analysis S800. First, each block 712 is checked for any marked breaks from the paper machine 100, in step S840. If a break has been marked for a block 712, the action score is set to one for that block 712 and the action footage is set to the next mark starting footage. For the blocks that do not have an action score set to one, the break analysis then proceeds to the next step S850 to check the sheet attributes. The process is then repeated for each of the remaining four analyses S860, S870, S880, and S890. Once all of these analyses has been performed, the break analysis S800 is then completed in step S831. We will now describe each of these analyses in turn.

Figures 9C, 9D, 9E:
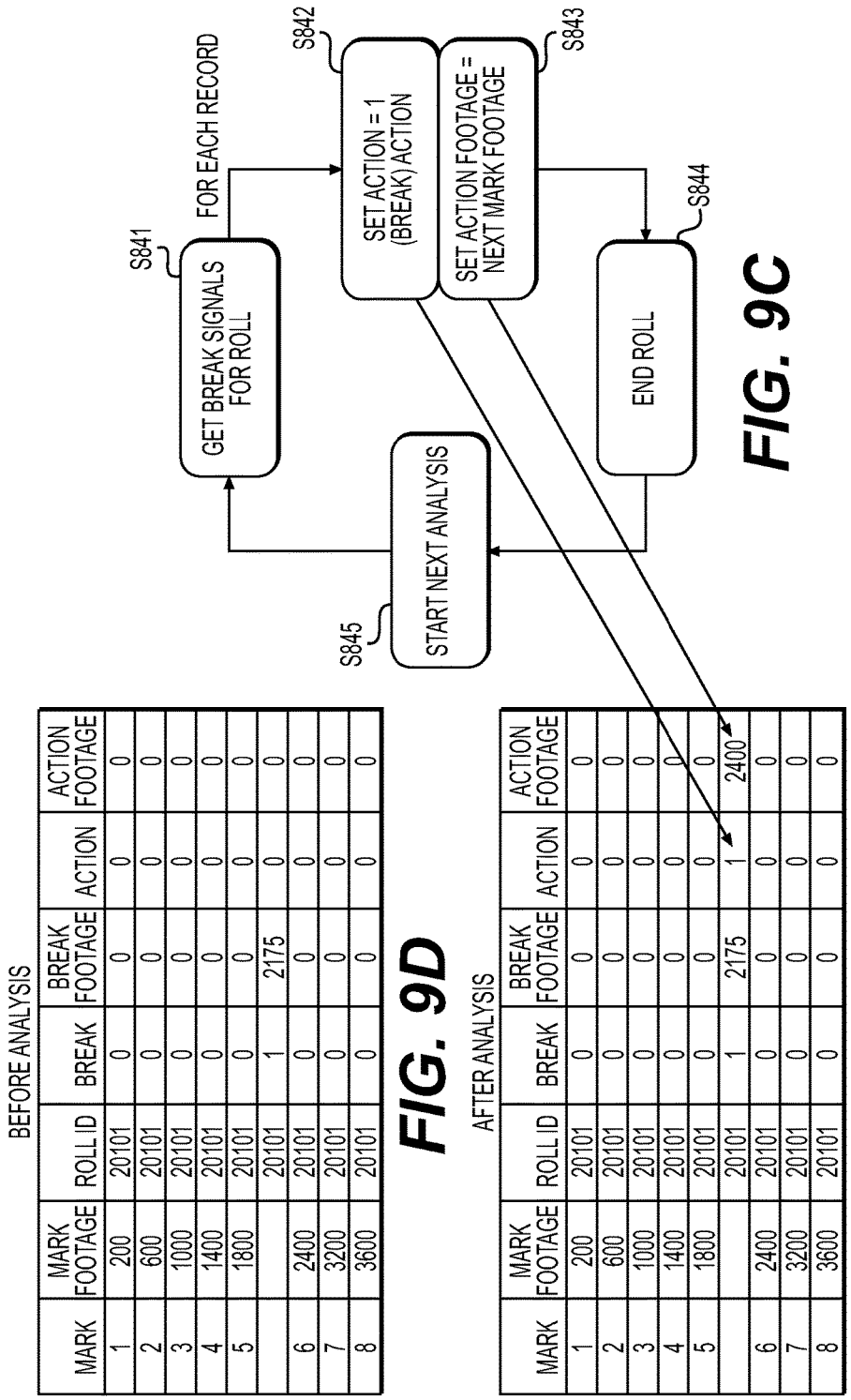

FIG. 9C is a detailed flow chart of the analysis for marked breaks S840. FIG. 9D is an example of a consolidated database before analysis, and FIG. 9E is the consolidated database after the marked breaks analysis S840 has been performed. First, in step S841, the current block 712 is checked to identify if any break signals have been recorded. As shown in FIG. 9D, a break signal has been recorded for the fifth mark with a linear footage of two thousand one hundred seventy-five feet. For this break, the action score is set to one in step S842 and the action footage is set to the next mark footage (in this case, mark six at two thousand four hundred feet) in step S843. Then, the analysis proceeds to step S844 where it determined if this block 712 is the end of the roll. If so, the next analysis is started in step S845. If not, the process is repeated for the next block 712. When no break signal is recorded, no change is made to the action score and action footage, and the analysis proceeds to step S844.

Figure 10A:
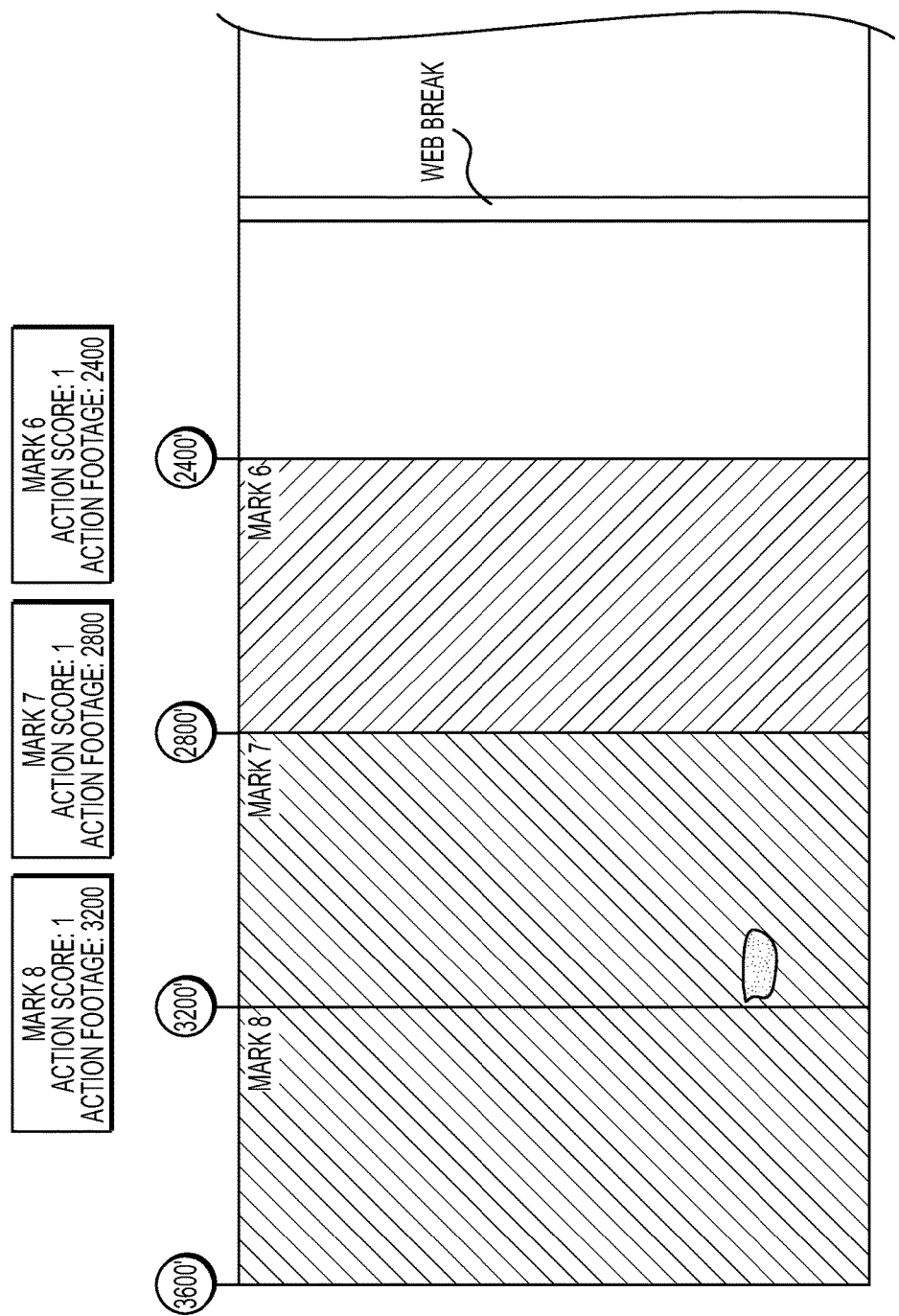
FIGS. 10A and 10B show a map of the scored database shown in FIG. 9N.
Figure 10B:
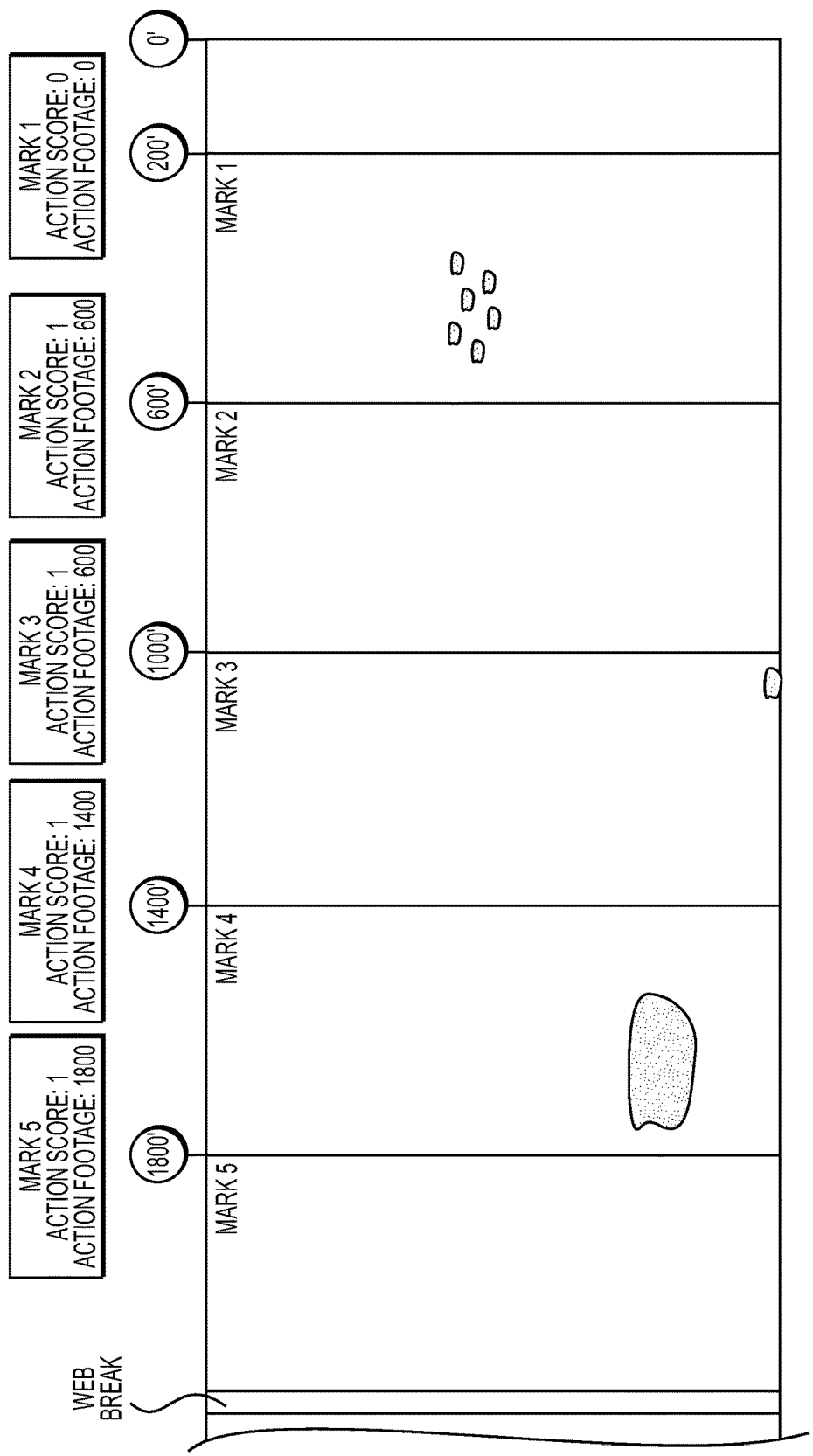

As discussed above, the linear footage is measured from the leading edge of the parent roll 190. This edge, however, is the last portion to be converted on the converting line because converting begins at the end of the parent roll 190. For this reason, each action analysis sets the action footage as the next mark footage and not the footage associated with the current block 712. As shown in FIGS. 10A and 10B, for example, the paper web 102 will be converted from left to right. Although the block associated with the fifth mark contains a web break, the web break would have already caused a converting line failure if the action score of one and action footage of one thousand eight hundred feet was not processed until the fifth mark was read. As a result, the sixth mark, which has an action footage of two thousand four hundred feet, is set to indicate the upcoming web break and not action footage one thousand eight hundred feet, which is associated with the fifth mark.

Figure 9F:
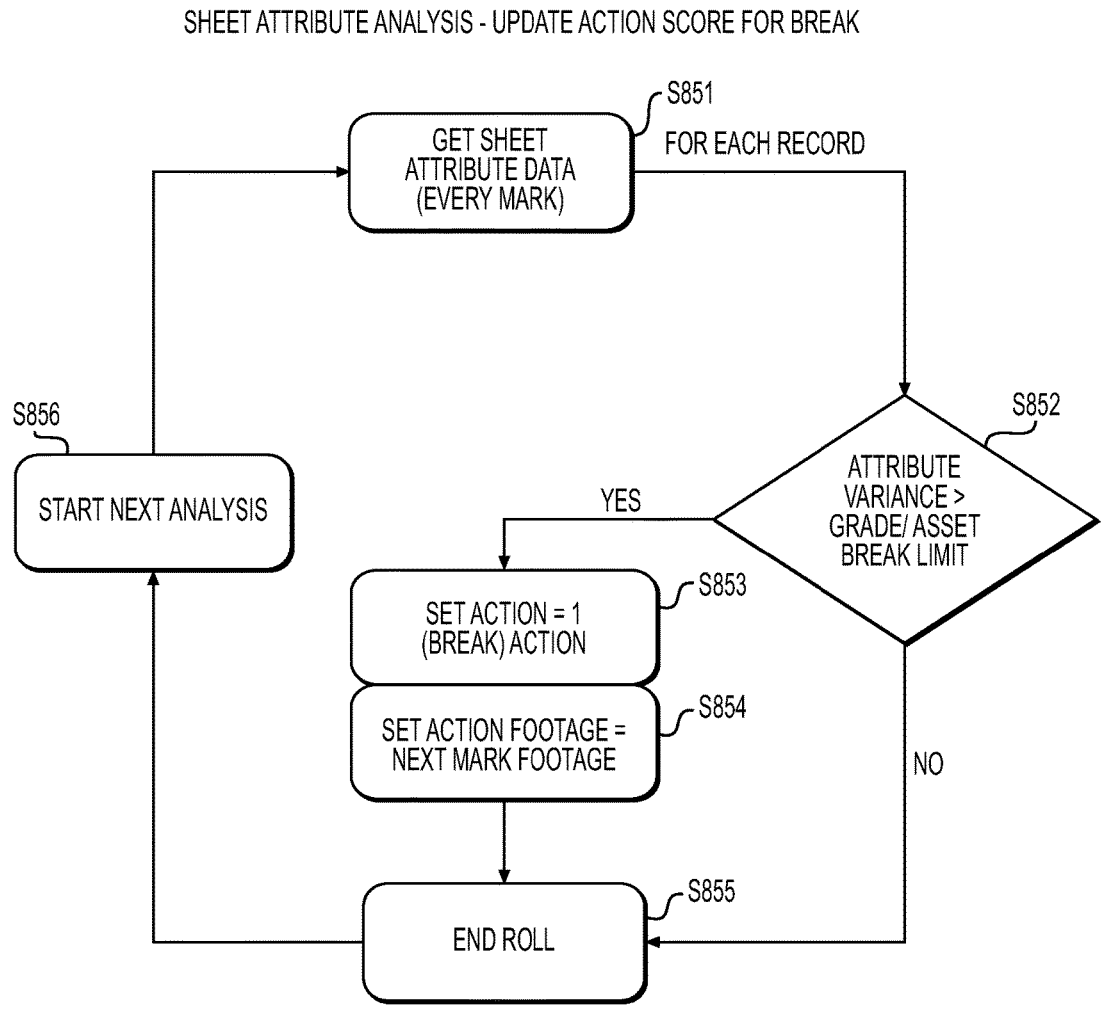

FIG. 9F is a detailed flow chart of the check sheet attributes analysis S850. First, the sheet attribute data for the current block 712 is obtained in step S851. Sheet attribute data may also be referred to as web properties and includes any aspect of the web that is not visible to the naked eye. Specific examples include those properties discussed above, such as basis weight, moisture content, and MD tensile strength. Each attribute being analyzed for the likelihood of failure is compared to a threshold value in step S852. Typically, each attribute has a target mean and a variance of the attribute for the current block 712 can be calculated compared to that mean. If the variance exceeds a break limit, the action score will be set to one in step S853 and the action footage set to the next mark footage in step S854. The analysis then proceeds to steps S855 and S856, which are similar to steps S844 and S845, respectively. If the variance is less than or equal to the break limit, no change to the action score will be made, and the analysis will proceed to steps S855 and S856. Different types of paper product will be converted differently and respond to a converting line differently. Compare, for example, tissue product to towel product. Even within a type of product, there are different grades, for example, towel product produced for commercial use compared to towel product produced for consumer use. The break limit for each attribute is thus set differently for different grades of product. Additionally, converting lines used to convert the same product may have differences, and thus, the break limit for each attribute may be customized for each different asset.

Figure 9G:
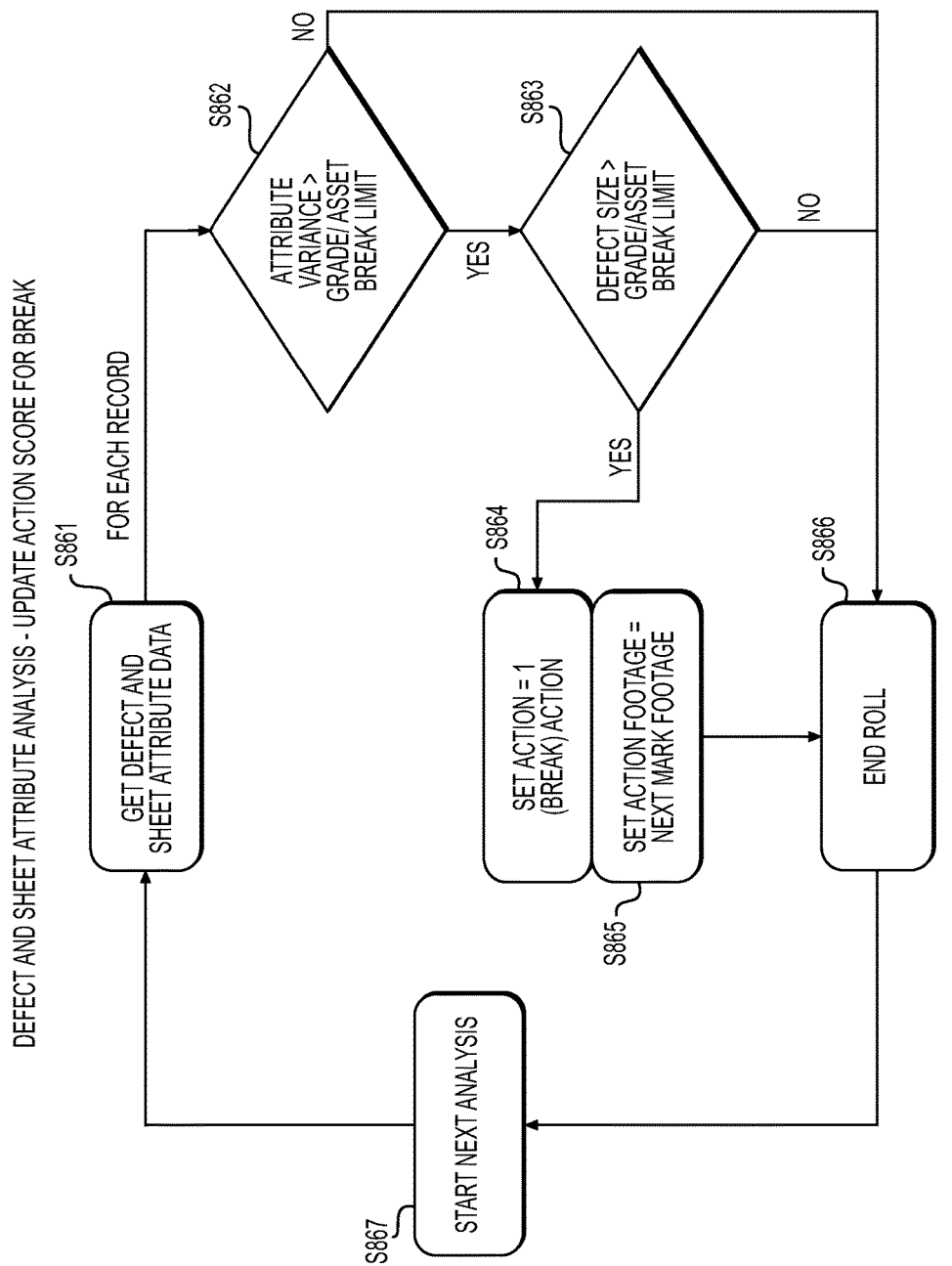

FIG. 9G is a detailed flow chart of the check defect and sheet attributes analysis S860. Even though the individual variance of an attribute did not exceed the break limit, some variances when combined with a defect could lead to a high likelihood of converting line failure. Both sheet attribute data for the current block 712 and the defect data for the record being analyzed are obtained in step S861. As shown in FIG. 9L and as discussed above, each defect is recorded in the consolidated database as its own record. For example, a small hole is recorded as data table entry number two. Then, the attribute data is compared to a break limit in step S862, similar to the comparison performed in step S852, but for a lower break limit. If the variance exceeds the break limit, the defect data is compared against a break limit. In this example, it is the size of the defect that is evaluated, but those skilled in the art will recognize that other defect criteria may also be evaluated, including those discussed below in conjunction with steps S870, S880, and S890. If the size of the defect exceeds the break limit, then the action score is set to one in step S864 and the footage is set to the next mark footage in step S865. The analysis then proceeds to steps S866 and S867, which are similar to steps S844 and S845, respectively, but before proceeding to the next block 712, each defect within the current block is analyzed. If either of the break limits is not exceeded, no action score is set and the analysis proceeds to steps S866 and S867.

Figure 9H:
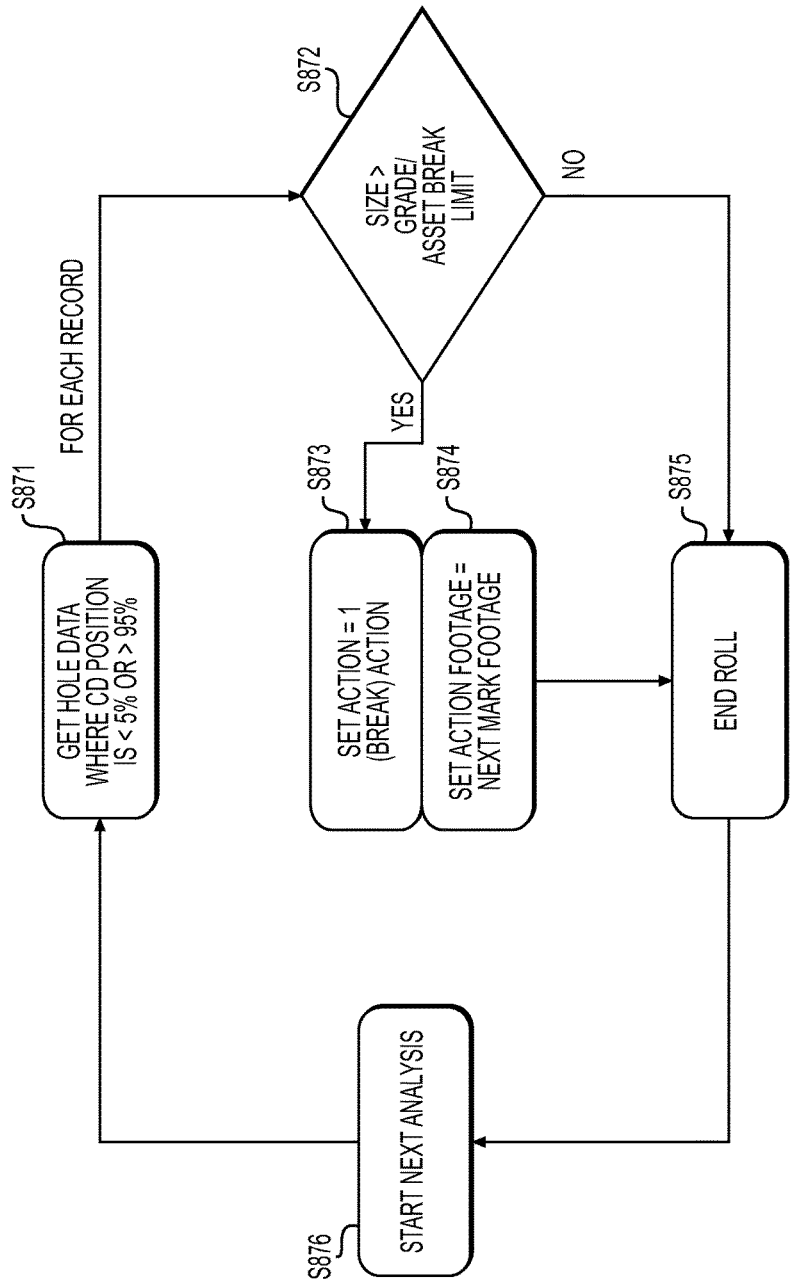

FIG. 9H is a detailed flow chart of the check edge defect analysis S870. A defect on the edge of the paper web will generally have a greater likelihood of resulting in a converting line failure than the same defect located toward the center of the sheet. Thus, a defect record, for the current block 712, having a position near the edge of the paper web is identified in step S871. In this embodiment, edge defects are those having a CD position located within the first five percent or the last five percent of the CD width (i.e., CD position is less than five percent or greater than ninety-five percent). Once the defects are identified, they are then compared to the break limit is step S872. If the size of the defect exceeds the break limit, then the action score is set to one in step S873 and the footage is set to the next mark footage in step S874. The analysis then proceeds to steps S875 and S876, which are similar to steps S866 and S867, respectively. If the break limit is not exceeded, no action score is set and the analysis proceeds to steps S875 and S876.

Figure 9I:
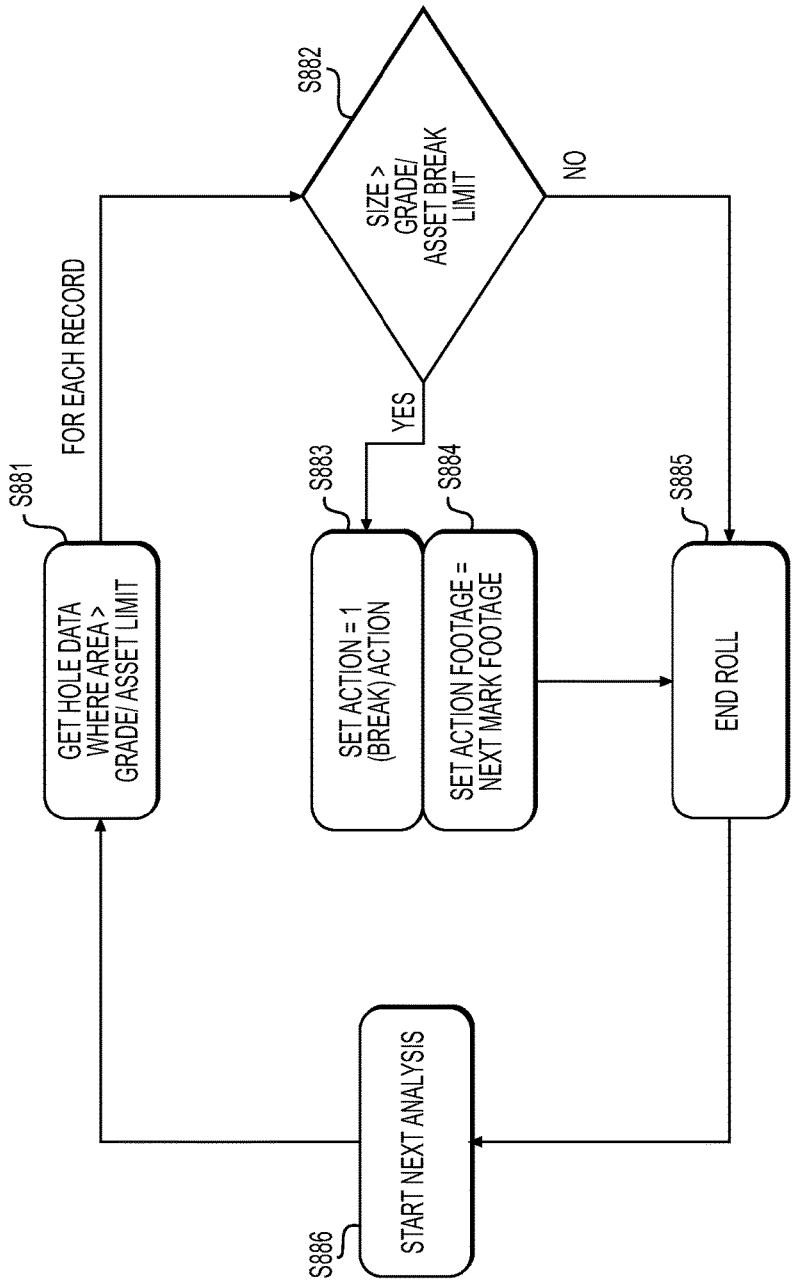

FIG. 9I is a detailed flow chart of the check single defect analysis S880. This analysis assesses the likelihood of converting line failure for a single defect. Here, a defect record for the current block 712 having a size greater than a limit is identified in step S881. The size is then compared to the break limit in S882. If the size exceeds the break limit, then the action score is set to one in step S883 and the footage is set to the next mark footage in step S884. The analysis then proceeds to steps S885 and S886, which are similar to steps S866 and S867, respectively. If the break limit is not exceeded, no action score is set and the analysis proceeds to steps S885 and S886.

Figure 9J:
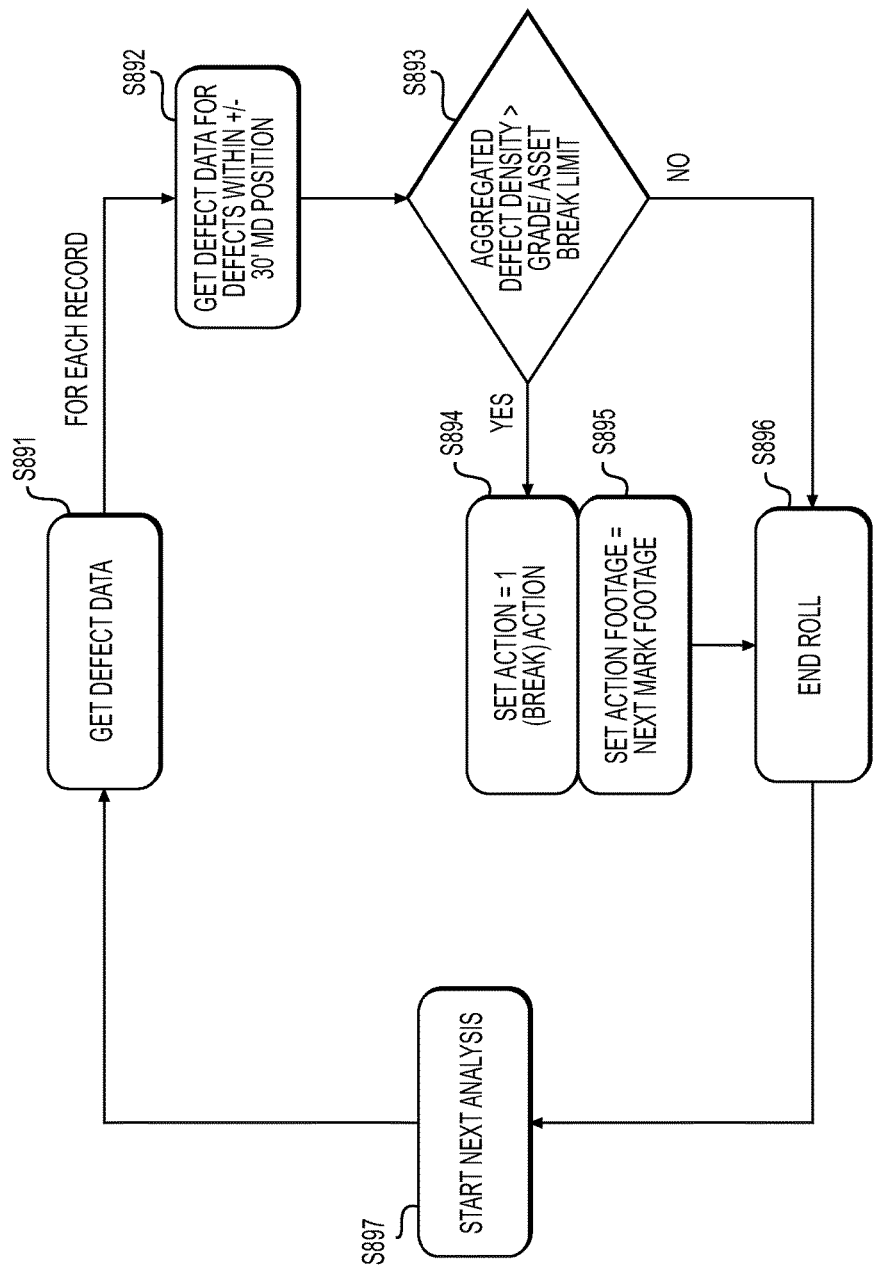

FIG. 9J is a detailed flow chart of the check cluster defect analysis S890. This analysis assesses the likelihood of converting line failure of a combination or cluster of defects. Here, a defect record (current record) for the current block 712 is obtained in step S891. Then, the defect data for records located within a certain distance of the current record (for example, within plus or minus thirty feet in the MD direction) are obtained in step S892. The density of the positions of these defects is compared to a break limit in step S893. If the density exceeds the break limit, then the action score is set to one in step S894 and the footage is set to the next mark footage in step S895. The analysis then proceeds to steps S896 and S897, which are similar to steps S866 and S867, respectively. If the break limit is not exceeded, no action score is set and the analysis proceeds to steps S896 and S897.

Figure 9K:
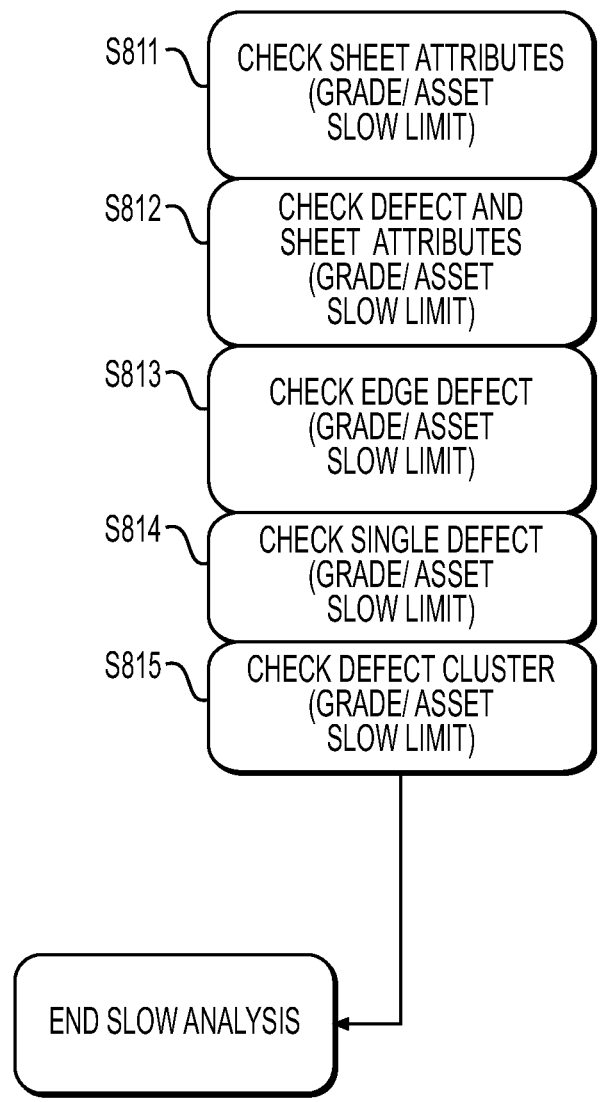

Once the break analysis is completed, the slow analysis is performed in step S810. FIG. 9K shows the analyses performed as part of the slow analysis. Each of the analyses S811, S812, S813, S814, and S815 is performed in a similar way as the corresponding break analysis, S850, S860, S870, S880, and S890, respectively. The limits for the slow analyses, however, are lower than the limits for the break analyses. The quality analyses S820 are also performed in a like manner.

FIG. 9L shows an example of a consolidated database prior to performing break analysis S800. FIG. 9M shows the consolidated database after performing break analysis S800. The defect records in the first mark correspond to a cluster of defects. The defect record in the third mark corresponds to an edge defect. The defect record in the fourth mark corresponds to a large defect. The data table entry fourteen corresponds to a web break signal as discussed above with reference to FIGS. 9D and 9E. The sixth mark has a low basis weight, and the seventh mark has a combination of a low basis weight and a defect. As will be discussed further below, the action score and the footage for the next block with a non-zero action score is sent for each mark to the converting line controller. Once the action score and quality score have been assigned for each block 712, the remaining marks are then updated to have the action score and action footage of block 712 with the next non-zero action score to result in the scored database. This database is shown in FIG. 9N. (FIGS. 10A and 10B are graphical illustrations of this database, similar to that shown in FIG. 4.)

We will now describe an alternative approach of inputs for converting line control using fault codes and severity levels, with reference back to FIG. 8. Because the likelihood of failure in one segment may be influenced by an adjacent segment, the likelihood of failure is determined over an analysis window 730. An analysis window 730 could be, for example, an individual block. In the preferred embodiment, the analysis window 730 encompasses multiple blocks 712. In this example, an analysis is being performed to assign fault codes and severity levels for the block 712 corresponding to analysis centerline 740. An additional advantage of an analysis window that encompasses multiple blocks is that some degree of smoothing can occur. As will be discussed further below, it is preferable to ramp down or to ramp up converting line parameters, instead of making sudden changes.

Then, for defects corresponding to one of the fault codes, a severity level may be established as a composite score from each of the analysis passes. For example, each block 712 of the consolidated database may be reviewed for a recorded web break that occurred on the paper machine 100 (FIG. 1). This type of defect is associated with a break fault code and each of the blocks 712 having this defect would be assigned a fault code of break with a severity level of ten. Next, each block 712 of the consolidated database may be reviewed for tears. Each block 712 having a tear would be assigned the fault code break with a severity level corresponding to the length of the tear. At a next pass, each segment 720 may be reviewed to determine if the number of defects or total size exceeds a threshold value. Various threshold values could be used, each corresponding to a different severity level for break fault codes. The next pass could expand the analysis window 730 to encompass adjacent blocks 712. Within the analysis window, a fault code of break could be assigned with a severity level when adjacent segments 720 contain a total number or total size of defects exceeding a threshold value. Again, various threshold values could be used, each corresponding to a different severity level for break fault codes. Once all of the analysis passes for defects to be assigned a break fault code are completed, a composite severity can be calculated when a block has been assigned two or more severity levels from the analysis passes.

The analysis process and severity level assignment may be modified by taking into account other web properties. For example, when a block 712 or, a segment 720 has a low basis weight, low tensile strength, or high moisture content, the severity level may be increased for that block 712. The process may then be repeated for other fault codes, such as wrap and quality.

Figure 11:
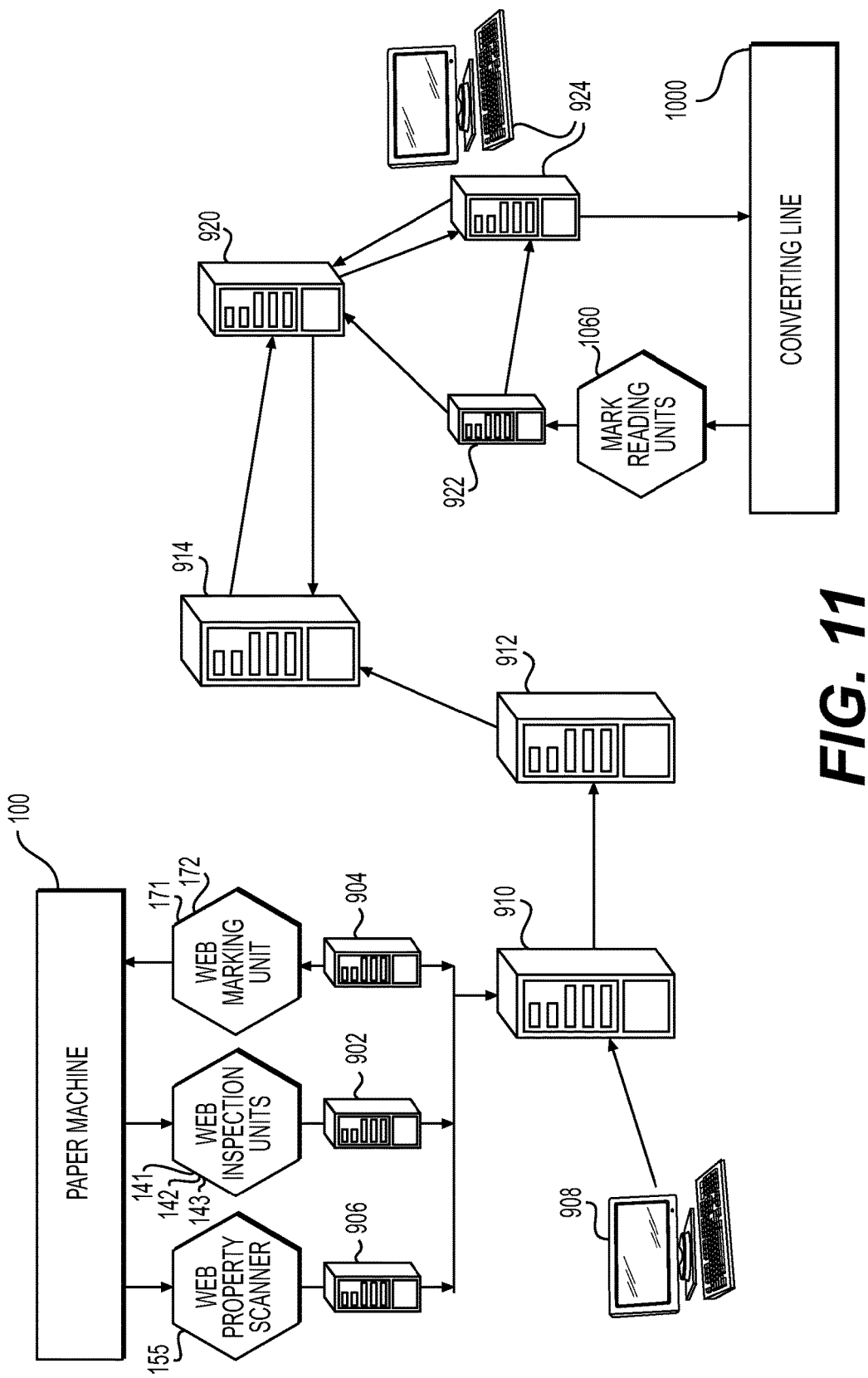
FIG. 11 is a system diagram of an embodiment of our invention.

The foregoing methods and processes for assigning inputs for converting line control by the analysis tool 912 may be implemented on a computer. A system diagram showing how the analysis tool 912 is interconnected to the paper machine and the converting line is depicted in FIG. 11. As discussed above (see FIGS. 1 and 2), the web inspection system, web marking unit 171, 172, and web property scanner 155 populate the defect database. The web inspection system may include web inspection units 141, 142, 143 connected to web inspection computer 902. Likewise, the web marking unit 171, 172 and the web property scanner 155 may also be connected to a web marking computer 904 and a web property computer 906, respectively. These three computers 902, 904, 906 are configured to process the inspection, marking, and property data, and then transmit the data to a database server 910 to populate the defect database. Additional web information that is collected offline may be added to the defect database to create the consolidated database through an offline input personal computer (PC) 908. The consolidated database may also be stored on the database server 910. The analysis tool 912 then retrieves the consolidated database from the database server to create the inputs for the converting line. As depicted in FIG. 11, the analysis tool 912 is its own computer, but alternatively, the analysis tool 912 may be implemented on the database server 910. Once the analysis is completed, the scored database is transmitted to a roll server 914 and stored on the roll server 914. The roll server 914 may also be implemented on the same server as the analysis tool 912 or database server 910. Upon the start of converting, a master converting line computer 920 retrieves the scored database from the roll server 914 to use in the converting process, which will be discussed further below. In this regard, we will discuss that the converting line retrieves the scored database by identifying a marked edge of the paper web 102.

The procedures depicted and discussed above with reference to the paper machine, offline input PC, database server, analysis tool, analysis tool, or any portion or function thereof, may be implemented by using hardware, software, or a combination of the two. Likewise, the procedures depicted and discussed below with reference to the converting line, or any portion or function thereof, may be implemented by using hardware, software, or a combination of the two. The implementation may be in one or more computers or other processing systems. While manipulations performed in these embodiments may have been referred to in terms commonly associated with mental operations performed by a human operator, no human operator is needed to perform any of the operations described herein. In other words, the operations may be completely implemented with machine operations. Useful machines for performing the operation of the embodiments presented herein include general purpose digital computers or similar devices.

Portions of the embodiments of the invention may be conveniently implemented by using a conventional general purpose computer, a specialized digital computer, and/or a microprocessor programmed according to the teachings of the present disclosure, as is apparent to those skilled in the computer art. Appropriate software coding may readily be prepared by skilled programmers based on the teachings of the present disclosure.

Some embodiments include a computer program product. The computer program product may be a non-transitory storage medium or media having instructions stored thereon or therein that can be used to control, or to cause, a computer to perform any of the procedures of the embodiments of the invention. As discussed above, the storage medium may include, without limitation, a floppy disk, a mini disk, an optical disc, a Blu-ray Disc, a DVD, a CD or CD-ROM, a micro drive, a magneto-optical disk, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the non-transitory computer readable medium or media, some implementations include software for controlling both the hardware of the general and/or special computer or microprocessor, and for enabling the computer or microprocessor to interact with a human user or other mechanism utilizing the results of the embodiments of the invention. Such software may include, without limitation, device drivers, operating systems, and user applications. Ultimately, such computer readable media further includes software for performing aspects of the invention, as described above.

Included in the programming and/or software of the general and/or special purpose computer or microprocessor are software modules for implementing the procedures described above.

Next, we will describe a converting line and control of the converting line for a preferred embodiment of our invention, with reference to FIGS. 12A to 14B. Parent rolls 190 (191, 192 in FIGS. 12A and 12B) are converted to consumer sized rolls and other products at a converting line. Our invention may be adapted to work with any number of different converting lines known in the art. One of the simplest forms of converting lines is for a single-ply paper towel product. Here, a paper web is unwound from a parent roll 191, 192 at an unwind stand 1010 and then rewound into a log 1080 at a rewinder 1076. A log 1080 is the width of a parent roll, but has the diameter of the consumer sized product. Also, at the rewinder 1076, the outermost end of paper web is glued by a tail gluer when the end is cut from the paper web feeding the rewinder. The log 1080 is subsequently cut into consumer length products using a log saw 1094. Those skilled in the art will recognize that a converting line may encompass more operations than described above. For example, the paper web may be embossed by passing through a nip defined between, for example, an embossing roller 1072 and an anvil roller 1074. Further, the paper web from two or more different parent rolls 191, 192 may be combined prior to being wound into a log 1080 in order to form a multi-ply sheet. Other converting lines may not create rolls of consumer products, but instead, cut the web after embossing to form flat products such as napkins, facial tissue, and the like. These types of converting lines use a folder 1078 instead of a rewinder 1076. In this application, we will use the term finisher to generically refer to a rewinder 1076, a folder 1078, and the like. Even among converting lines established to make the same product, the equipment may differ. For example, some unwind stands 1010 may hold a single parent roll 191, 192, but others may hold two parent rolls 191, 192 and have the capability to switch between parent rolls 191, 192 without stopping the converting line. Switching between parent rolls 191, 192 may be accomplished through the use of a flying splice, as is known in the art, and will be discussed in more detail below. FIGS. 12A and 12B show schematic diagrams of an exemplary unwind stand 1010 having a flying splice.

FIG. 12A, thus, is a schematic diagram of an exemplary unwind stand 1010 and rewinder 1076. Parent rolls 191, 192 are placed on each of the roll mounts 1011, 1012. Each parent roll is driven by a motor 1013, 1014 that is connected to the parent roll 191, 192 through the use of drive belts 1015, 1016. The paper web 102 is being drawn from parent roll 191 and rewound in rewinder 1076 to create log 1080. The paper web 102 is conveyed over a series of rollers 1041, 1043, 1045, 1046, and 1050 between parent roll 191 and rewinder 1076. The depicted unwind stand 1010 is capable of performing a flying splice to switch from parent roll 191 to parent roll 192. To perform a flying splice, parent roll 192 is brought up to the speed of parent roll 191 by motor 1014. While the parent roll 192 is being brought up to speed, paper web 103 is being rewound on recovery roll 1022. (Recovery roll 1021 is used in the same way as recovery roll 1022 when switching from parent roll 192 to parent roll 191.) When splicing between parent rolls, press rollers 1031, 1032 bring paper web 102 together with paper web 103, and cutters 1033, 1034 are used to sever the paper web 103 from the recovery roll 1022 and paper web 102 from the rewinder 1076. Once the paper web 103 for log 1080 is being drawn from parent roll 192, parent roll 191 may be replaced with another parent roll or a portion of the paper web 102 having a defect may be removed. In the converting line depicted in FIG. 12A, the paper web 102 is embossed as it travels through a nip formed between and embossing roller 1072 and an anvil roller 1074. After being wound into a log 1080, the log is transferred to an accumulator 1092 before being cut into consumer sized lengths by a log saw 1094. The consumer size products are then packaged for distribution and sale by subsequent packaging equipment 1090.

Figure 12B:
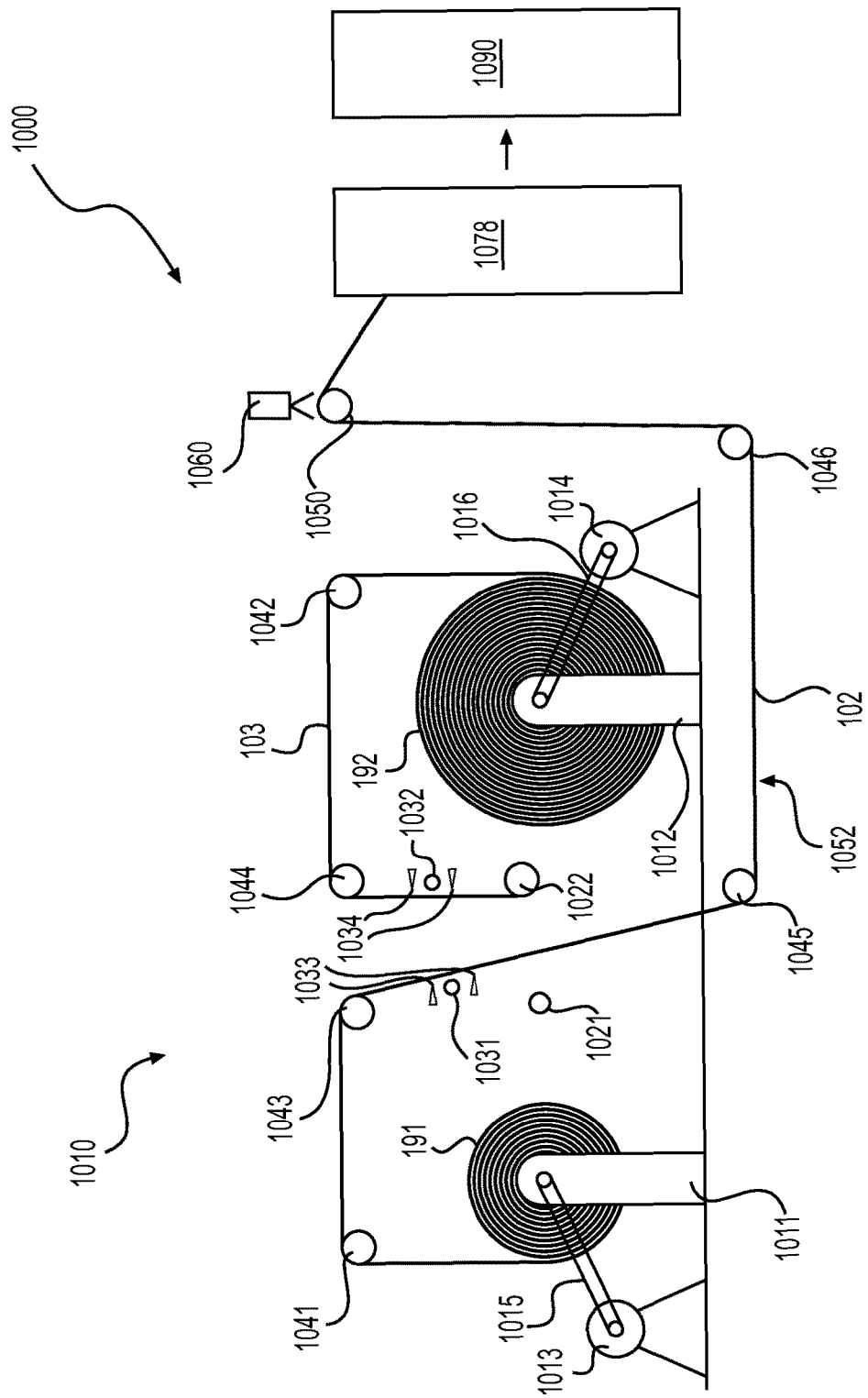

FIG. 12B is a schematic diagram of another exemplary converting line. This converting line is similar in operation to the converting line depicted in FIG. 12A, but includes a folder 1078 to produce folded consumer products such as napkins, tissues, and the like, instead of a rewinder 1076.

Converting lines are conventionally classified into class one and class two converting lines. Class one converting lines typically operate at a speed of about two thousand feet per minute for bath tissue and about two thousand seven hundred feet per minute to about three thousand feet per minute for towel products. Class two converting lines typically operate in the range of about one thousand three hundred feet per minute to about one thousand seven hundred feet per minute for all products.

In the preferred embodiment, the converting line 1000 is controlled through the use of a programmable logic controller (PLC) 924 (FIG. 11). In the discussion below, we will discuss the automated control of the converting line by referencing adjusting the converting line speed, splicing between parent rolls, and stopping the converting line. Those skilled in the art will recognize, however, that there are numerous parameters that can be controlled by the PLC 924 on the converting line, including tension between rollers and nip parameters, such as a gap between the rollers comprising the nip. Our invention may be readily adapted to control any number of these parameters, either individually or in concert with the other parameters.

In the embodiment shown in FIGS. 12A and 12B (with periodic reference to FIGS. 6, 7 and 11), a mark reading unit 1060 is positioned shortly after the location where the paper web 102 is unwound from parent roll 191. The mark reading unit 1060 is positioned to inspect the edge of the parent roll 191 and to read any mark 610, 620 that passes. In the preferred embodiment, the mark reading unit 1060 includes at least a digital high speed camera to read the mark and a light to illuminate the edge of the paper web 102. Any suitable high speed camera may be used in the mark reading unit 1060. Further, any suitable light source may be used, such as a light-emitting diode (LED), an incandescent light, and the like. When ink that is visible under ultraviolet light is used, an LED light source emitting light in the ultraviolet spectrum is preferred. The mark reading unit 1060 is preferably placed at a stable location on the unwind stand 1010 or rewinder 1076. Suitable locations include, for example, flat surfaces (e.g., web run 1052) and rolls (e.g., roll 1050). In the preferred embodiment shown in FIGS. 12A and 12B, roll 1050 is a bowed roll. A bowed roll has an offset axis of rotation, which stretches the paper web 102, 103 toward the ends of the roll. This roll may also be called a spreader roll, as it spreads the paper. As a result, the bowed roll 1050 helps to ensure that paper web 102, 103 is taut and moving at a consistent speed as it moves under the mark reading unit 1060. The mark reading unit 1060 is connected to a mark reading computer 922, which performs the mark identification analysis.

When a parent roll 191, 192 is loaded onto the unwind stand 1010 in the converting line 1000, an operator may manually enter the roll identification numbers into the PLC 924, which is then transmitted to the master converting line computer 920. Alternatively, the mark reading unit 1060 and mark reading computer 922 may identify the parent roll 191, 192 by reading a roll identification mark 610. Preferably, a parent roll 191, 192 is identified by reading the same roll identification number multiple times to ensure statistical confidence of the number read. Most preferably, the roll identification number is read twice from two sequential roll identification marks 610. Once the parent roll 191, 192 is identified, the parent roll identification number is transmitted to the master converting line computer 920. In either case, the master converting line computer 920 then retrieves from the roll server 914 the scored database associated with the identified parent roll 191, 192. When the roll server 914 transmits the scored database, the database is "checked out" from the roll server 914, and the scored database is "checked in" once the parent roll 191, 192 has been converted.

As the parent roll 191, 192 is unwound, the mark reading unit 1060 reads the mark 610, 620 on the paper web 102 and passes the information to the PLC 924. When roll identification information is read, the PLC 924 checks to ensure that the correct parent roll 191, 192 is identified. When location information is read, the PLC 924 adjusts the converting line parameters based on the inputs for converting line control associated with that block 712 identified in the scored database.

We will now describe converting line control using the preferred embodiment of an action score and a quality score. In this approach, each time a location mark 620 is read, the master converting line computer 920 transmits to the PLC 924: (1) the location information in linear feet associated with that mark (MD Footage), (2) the linear footage of the next block 712 of the paper web 102 that has a non-zero action score, (3) the action score of the next non-zero block 712 of the paper web 102, and (4) the quality score for the block 712 associated with the mark just read. The PLC 924 continuously counts the linear footage of the paper web 102 being converted. This count is updated upon receipt of the location information associated with the mark just read. The PLC 924 then calculates the distance remaining to the next non-zero block 712. The PLC 924 will also calculate, given the current operating parameters (for example, speed), the distance required to execute the action associated with the next non-zero block 712. The PLC 924 includes several factors in this calculation, depending upon the next action and specific converting line. These factors include: deceleration rate for a splice, deceleration rate for stopping, deceleration rate to slow, target speed for slowing, and the like. The PLC 924 then compares the distance remaining to the next non-zero block 712 to the calculated distance required to execute the next action. If sufficient footage is still available, the PLC 924 will continue converting at the current operating parameters and repeat the calculation. The PLC 924 will initiate the next action when the current footage is within a buffer distance of the calculated footage for the next action. We have found that it is beneficial to include buffer footage to prevent unintended web breaks from occurring because the PLC 924 waited to initiate action until there is exactly the amount of footage required between the current location and the next action point.

Figure 13:
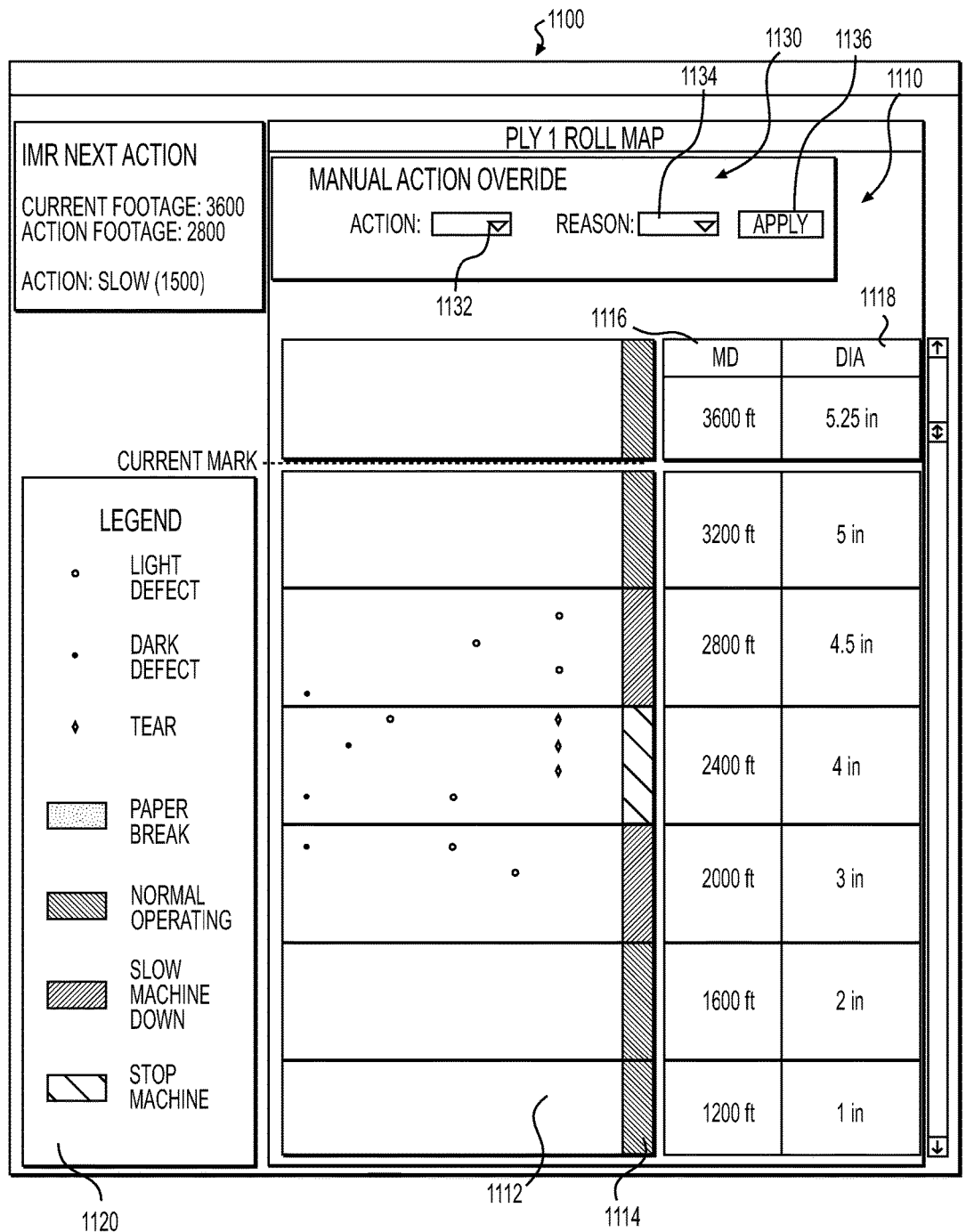
FIG. 13 shows a control screen for a converting line programmable logic controller that can be used in conjunction with our invention.

FIG. 13 shows an exemplary operator control screen 1100 for the converting line PLC 924 that may be used with this implementation. The control screen 1100 may be implemented on any suitable device including, for example, a touch screen or an LED display that is operated by a mouse and a key board. The control screen includes a roll map 1110. In this case, the roll map shows the first ply of a roll used in making a multi-ply paper product. The roll map includes a defect map 1112. The defect map 1112, like the defect map shown in FIG. 4, above, contains graphical indications of defect positions. Each line in the defect map 1112 indicates a different block 712 (FIG. 7). The action score associated with each block 712 is also identified on the defect map 1112. While any suitable means of indication may be used, a colored box 1114 is along the side of each block is used in this embodiment. Here, an action score of zero is indicated by a green box 1114 and corresponds to normal operation of the converting line. An action score of one results in a stop or a splice command and is indicated by a red box 1114. An action score of two slows the converting line and is indicated by a yellow box 1114. A legend 1120 is provided to describe the graphical indications of defects and the converting line actions associated with the colored boxes 1114. Also shown in the roll map 1110 is the MD footage 1116 associated with each block 712 and, as an operator aid, the diameter 1118 of the parent roll 190.

The control screen 1100 also allows for manual action overrides in a section 1130 of the control screen. The operator may review the upcoming blocks 712 and manually override the action score for that block. The operator may select a particular block 712 and then choose from preset actions in a drop down menu 1132. This section 1130 also includes a drop down menu 1134 for the operator to give a reason for his/her change. These reasons may subsequently be used to adjust the rules for assigning converting line control as discussed below. Once the operator has selected an action and a reason for the change, the operator then selects the apply button 1136. When the apply button 1136 is selected, the PLC 924 the updates the scored database with the manually applied action. We have found that it is beneficial to assign an alternate score (e.g., a three, a four, or a five) for manually input actions. This improves subsequent analysis and feedback used in refining the rules used to assign the action scores and quality scores. A status section 1140 is also displayed on the control screen 1100. This section 1140 gives an indication of the current footage, the footage at which the PLC will take the next action (action footage), and the next action.

We will now describe converting line control using the alternate converting line inputs of defect code and severity levels. When defect code and severity level are used, the PLC 924 adjusts the converting line parameters according to a predetermined set of rules. These rules are established for each converting line to prevent a converting line failure. For example, the PLC 924 may slow the converting line from about two thousand feet per minute to about one thousand five hundred feet per minute for a defect code for holes having a severity level of five, or slow the converting line to about one thousand two hundred feet per minute for holes having a severity level of seven. The actions taken by the PLC 924 to adjust parameters may vary by converting line. Using the example of a defect code for a web break, the PLC 924 on one converting line may execute a splice to switch between parent rolls, because the converting line has a flying splice capability, but the PLC 924 for a second converting line may stop the converting line for the same defect code.

In the preferred embodiment shown in FIGS. 12A and 12B, the mark reading unit 1060 is positioned downstream from the parent roll 191 being unwound. A particular block 712 (FIG. 7) of the paper web 102, therefore, has already traveled through a portion of the converting line 1000 before the location information associated with that block 712 is read. If that particular block has defects, they may cause a web break as the web passes one of the rollers 1041, 1043, 1045, 1046 upstream of the mark reading unit 1060. In this preferred embodiment, the PLC 924, therefore, sets the operating parameters of the converting line 1000 based on the defect code and severity level for a predetermined number of blocks 712 after the block 712 associated with the mark just read.

Figure 14:
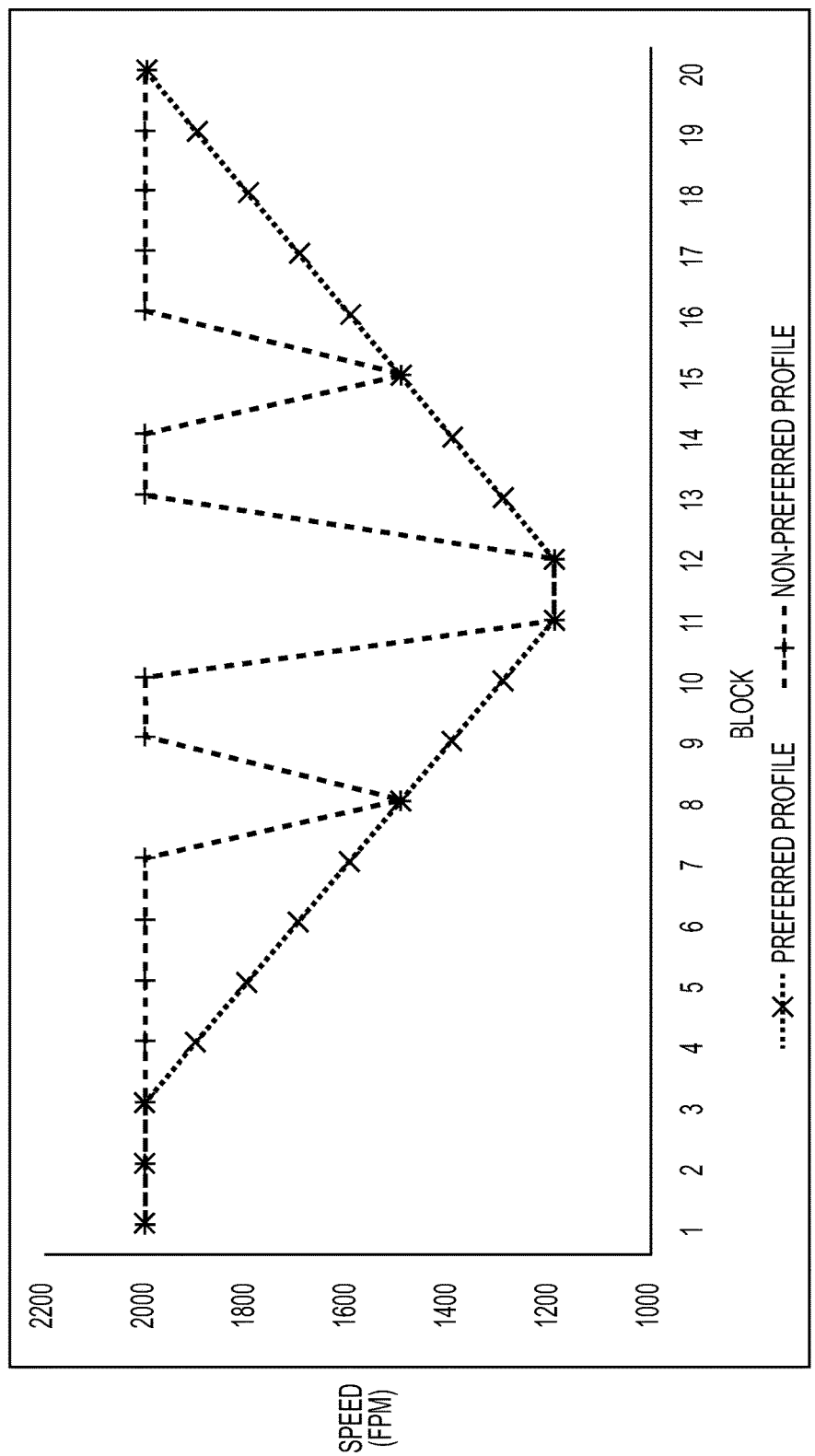
FIG. 14 is a graph showing an example of a preferred speed profile and a non-preferred speed profile for a converting line.

The PLC 924 may also consider several of the upcoming blocks in determining how the converting line parameters are adjusted. As shown in FIG. 14, blocks eight and fifteen may have defects requiring the converting line to slow to about one thousand five hundred feet per minute, and blocks eleven and twelve may have defects requiring the converting line to slow to about one thousand two hundred feet per minute. To avoid rapid and successive changes in operating speed (non-preferred profile in FIG. 14), the PLC 924 may begin slowing the converting line at block four to reach about one thousand five hundred feet per minute at block eight and about one thousand two hundred feet per minute at block eleven, and then gradually increase speed from block twelve to reach full speed of about two thousand feet per minute at block twenty (preferred profile in FIG. 14). Those skilled in the art will recognize that the assignment of operating parameters may be performed by the analysis tool and pushed to the converting line, instead of being performed at the converting line.

Figure 15A:
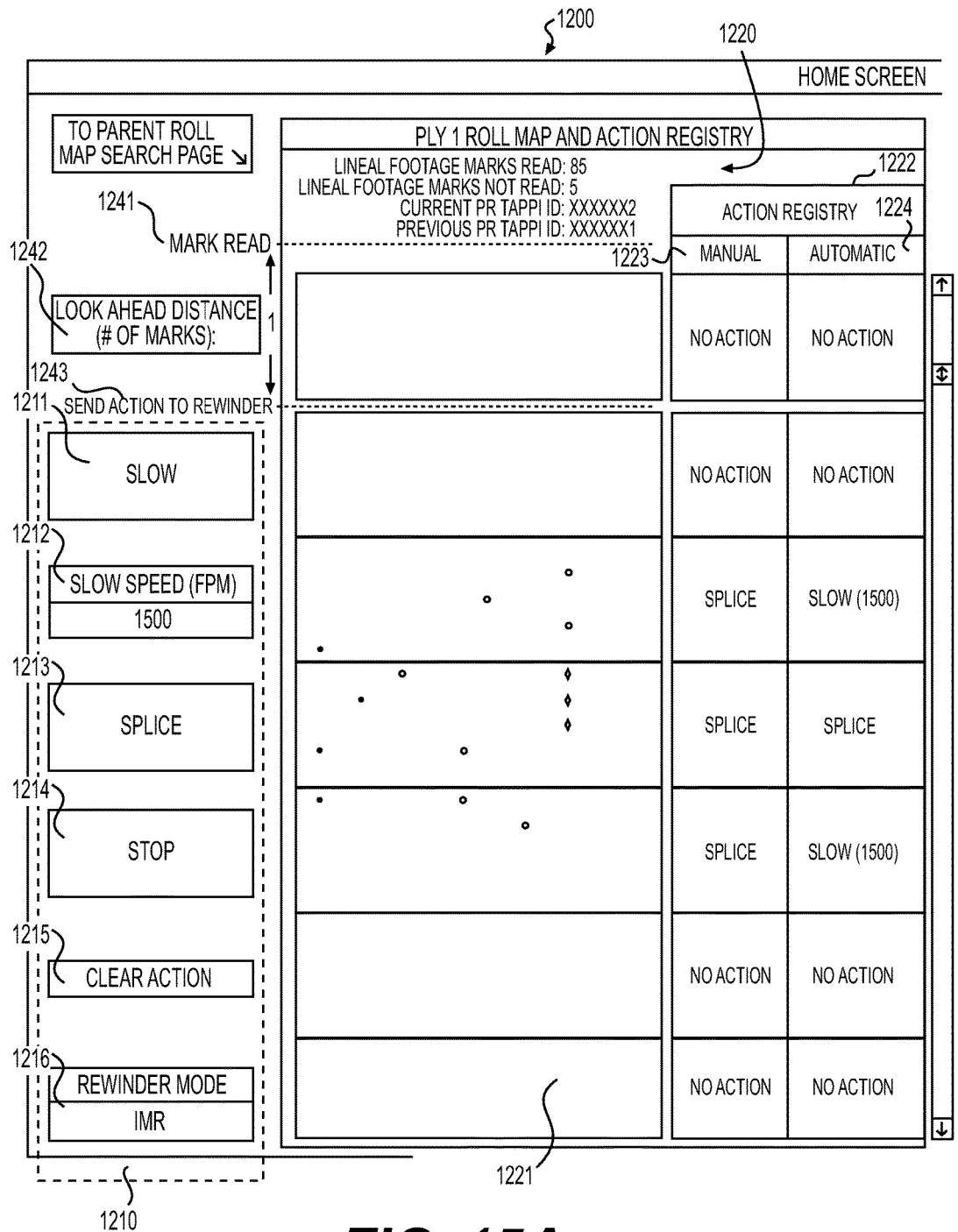
FIGS. 15A and 15B show an alternate control screen for a converting line programmable logic controller that can be used in conjunction with our invention.
Figure 15B:
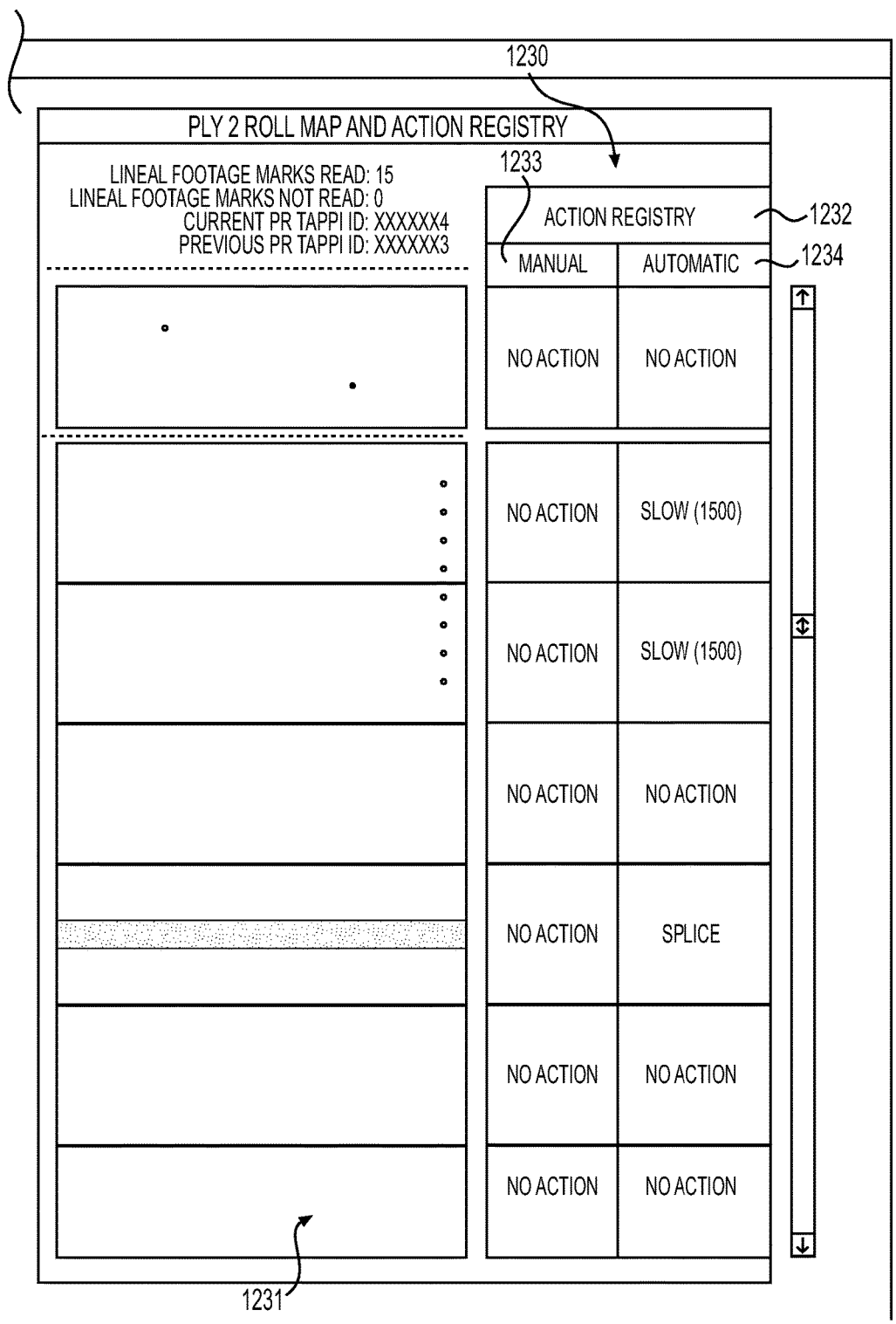

FIGS. 15A and 15B show an exemplary operator control screen 1200 for the converting line PLC 924. FIG. 15A shows the left half of the control screen 1200 and FIG. 15B shows the right half. In this embodiment, the converting line is creating a two-ply paper product and uses two parent rolls, one for the first ply and the other for the second ply. As with control screen 1100, the control screen 1200 may be implemented on any suitable device including, for example, a touch screen or an LED display that is operated by a mouse and a keyboard. The control screen 1200 has three major sections: operator controls 1210, the first ply roll map and action registry 1220, and the second ply roll map and action registry 1230. Each roll map and action registry 1220, 1230 contains a defect map 1221, 1231. The defect map, as with the defect map shown in FIG. 4, above, contains graphical indications of defect positions. Each line in the defect map 1221, 1231 indicates a different block 712 (FIG. 7). Each action registry 1222, 1232 contains two sub-registries. The first is an automatic action registry 1224, 1234. This registry contains the actions assigned to each block 712 by the PLC 1024 based upon the defect code and severity level. The second is a manual action registry 1223, 1233. The control screen 1200 allows an operator to review upcoming blocks 712 and to input manual actions in the manual action registry 1223, 1233. An operator may change input actions by selecting a block 712 and then choose one of the operator controls 1210. An operator may specify a slower speed by inputting the speed into the slow speed set point 1212 and then pressing the slow button 1211. Alternatively, the control screen may have only one slow speed preset. The operator may input a splice or a stop by pressing the splice button 1213 or stop button 1214, respectively. The operator may clear the manually inputted action by pressing the clear action button 1215. The PLC 924 will control the converting line by the actions in the automatic action registry 1224, 1234 unless overridden by an action in the manual action registry 1223, 1233.

In the present embodiment, the PLC 924 takes the actions assigned to a block 712 that is a predetermined number of blocks 712 behind the mark read by the mark reading unit 1060, as discussed above. On the control screen 1200 shown in FIGS. 15A and 15B, this is illustrated by mark read line 1241 and send action line 1243. The operator may select a predetermined number of blocks by changing values assigned to the look ahead distance 1242. In this embodiment, when a two-ply paper product is being created on the converting line 1000, the speed for the converting line will be set for a particular segment by the slowest speed in the active action registry for either ply. When there is a splice, however, the action will be taken for only one parent roll.

Figure 16:
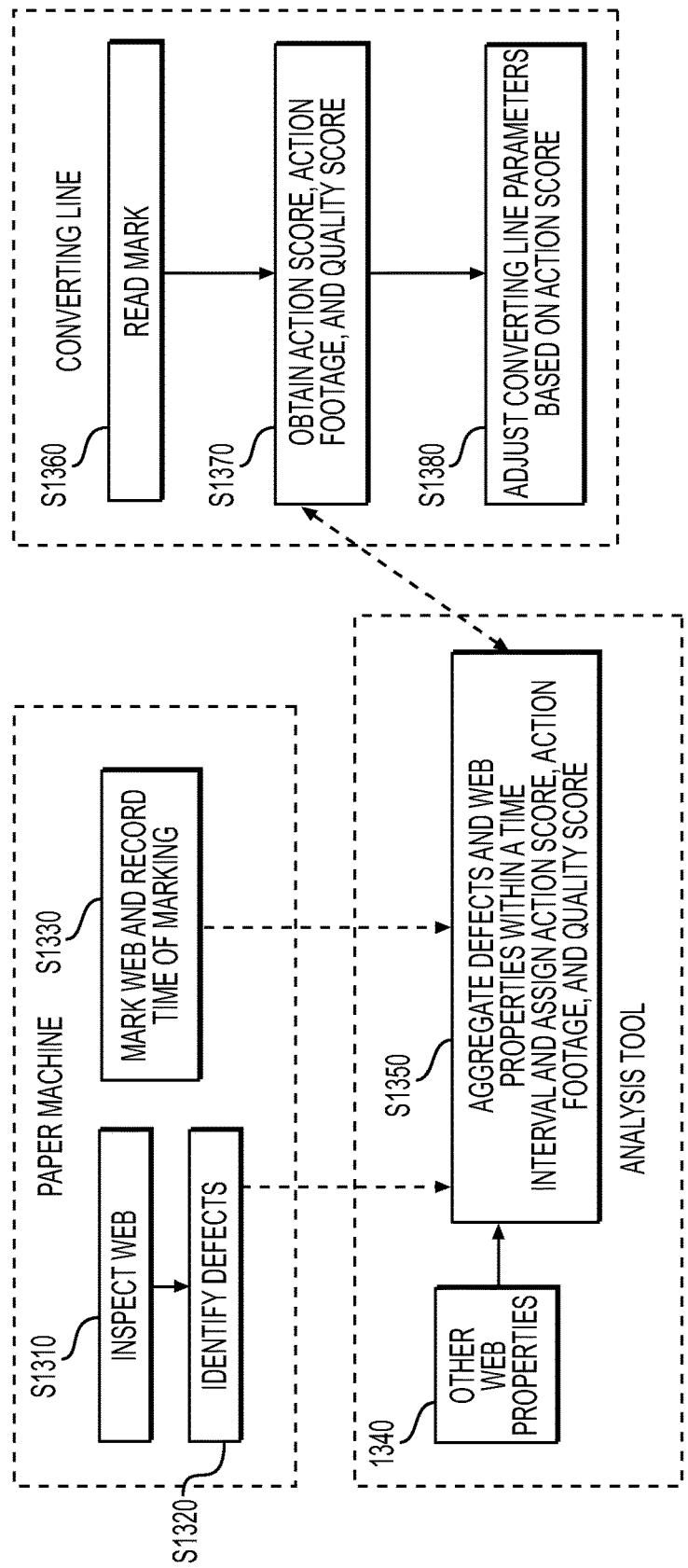
FIG. 16 is a flow chart of an embodiment of our invention.

We will now describe a preferred embodiment of our invention with reference to FIGS. 16 to 19. In this preferred embodiment, the inputs assigned and used for converting line control are the action score and quality score. FIG. 16 is a flowchart showing an overall process flow of our invention. As described in the embodiments discussed above, our invention is implemented to a paper machine 100, an analysis tool, and a converting line 1000. Those skilled in the art will recognize that the analysis tool may be co-located at either the paper machine 100 or converting line 1000 or may be at a separate location. In our invention, a web is inspected at step S1310 and the results of the inspection are used to identify defects in the web at step S1320. Also, at the paper machine 100, the web is periodically marked and both the mark 210 and the time of marking is recorded in step S1330. In step S1350, other web properties 1340, such as tensile strength and basis weight (discussed above), are used to aggregate the defects identified in step S1320 over a particular time interval. Also, in this step S1350, inputs for converting line control (i.e., action score and quality score in this embodiment) are assigned to a mark 210 applied to the web in step S1330. On the converting line 1000, the marks are read in step S1360. The action score, action footage, and quality score assigned to the read mark 210 are obtained in step S1370. In step S1380, the converting line parameters, such as converting line speed, are adjusted based upon the inputs obtained in step S1370.

Figure 17:
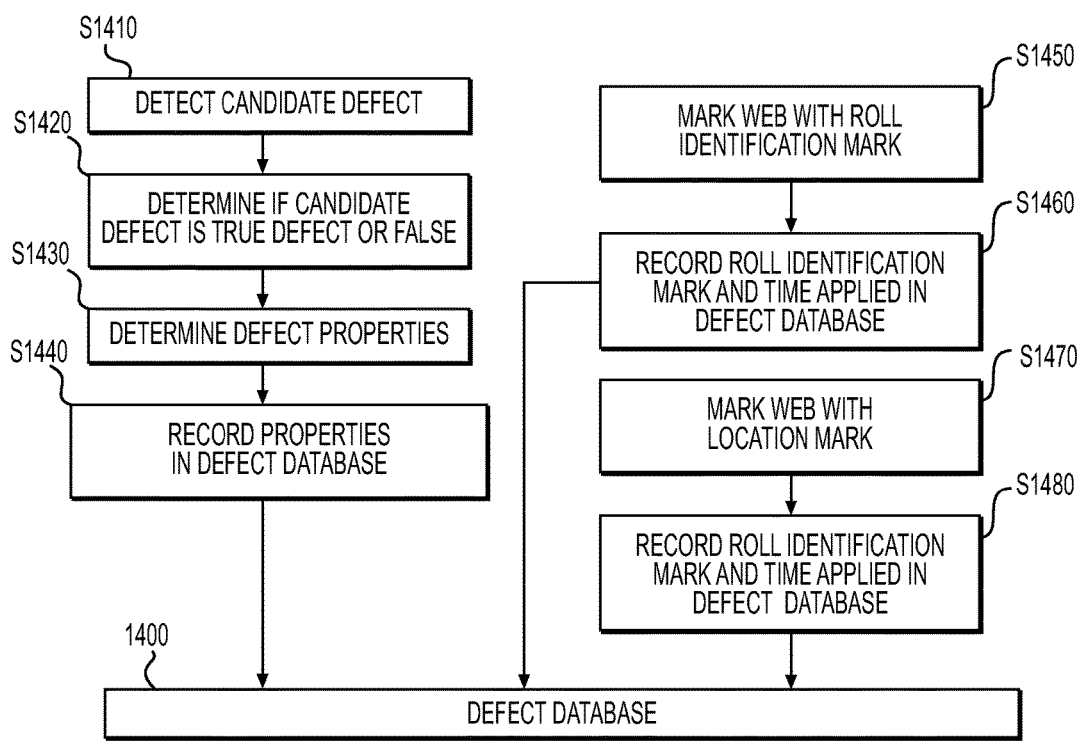
FIG. 17 is a detailed flow chart of process steps at a paper machine for the embodiment shown in FIG. 16.

Steps S1310, S1320, and S1330 shown in FIG. 16 will now be described in more detail with reference to FIG. 17. In step S1410, the web inspection system detects candidate defects. The web inspection system then determines whether the candidate defect is a true defect or a false defect using, for example, the method described in U.S. Patent Appln. Pub. No. 2012/0147177 (the disclosure of which is incorporated by reference in its entirety). For those defects that are true defects, the defect properties such as size and position are determined by the defect inspection system in step S1430. These defect properties for each true defect are then recorded in defect database 1400. The web is also marked with a roll identification mark 610 at a set periodicity by a web marking unit 171, 172 in step S1450. In step S1460, the roll identification mark 610 and the time the mark is made on the web is then recorded in defect database 1400. Similarly, the web is marked with a location mark 620 in step S1470, and then, in step S1480, this mark 620 and time of marking is recorded in defect database 1300. In the single mark embodiment, steps S1470 and S1480 may be omitted.

Figure 18:
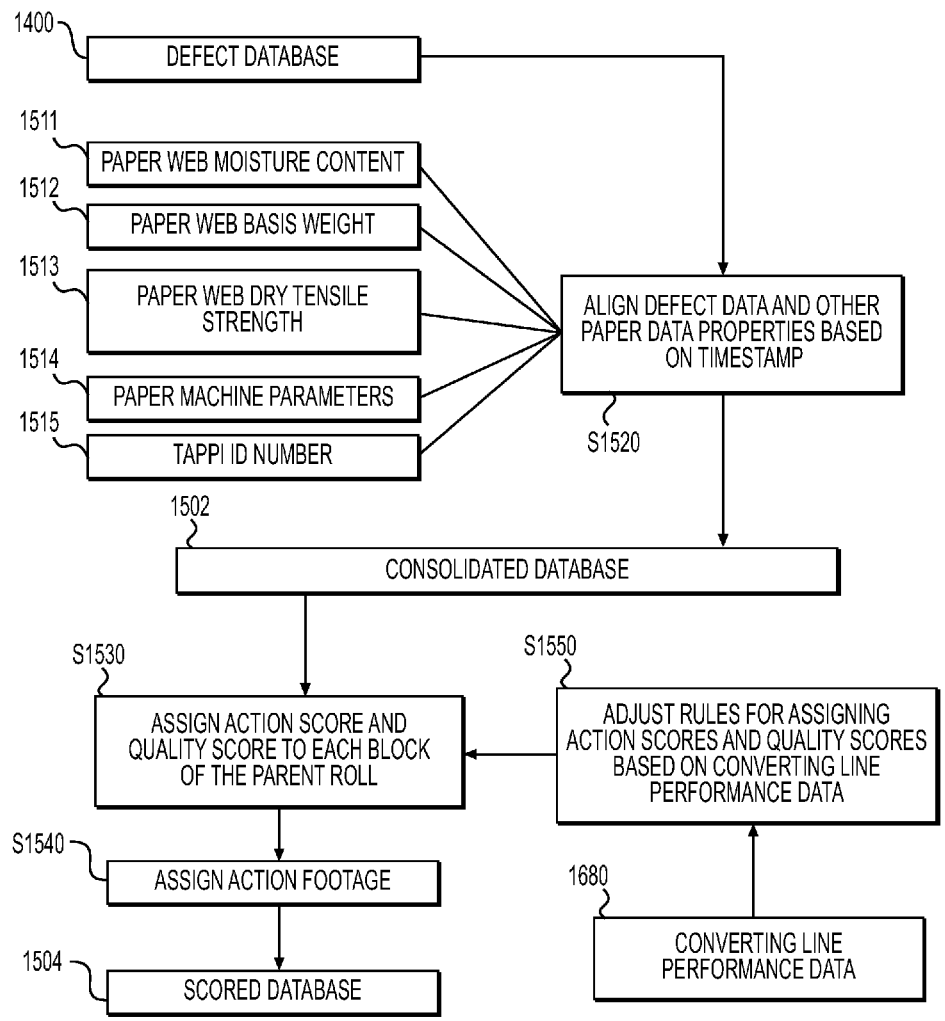
FIG. 18 is a detailed flow chart of process steps performed by an analysis tool for the embodiment shown in FIG. 16.

Step S1350 shown in FIG. 16 will now be described in more detail with reference to FIG. 18. In step S1520, the defect data from the defect database 1300 and other paper web properties such as paper web moisture content 1511, paper web basis weight 1512, paper web tensile strength 1513, the paper machine parameters used to derive web properties 1514, and TAPPI ID number 1514 are aggregated into a database and aligned in step S1530 within the database according to the master timestamp to form a consolidated database 1502. The consolidated database is then analyzed in step S1530 according to a predetermined set of rules to assign the action scores and quality scores to each block of the parent roll. Step S1530 may be executed using the process described above in reference to FIGS. 9A to 9M. Then, as described in reference to FIG. 9N, the action footage is assigned in step S1540 to form the scored database 1504. These rules may be adjusted periodically in step S1550 based upon performance data 1680 from the converting line 1000.

Figure 19:
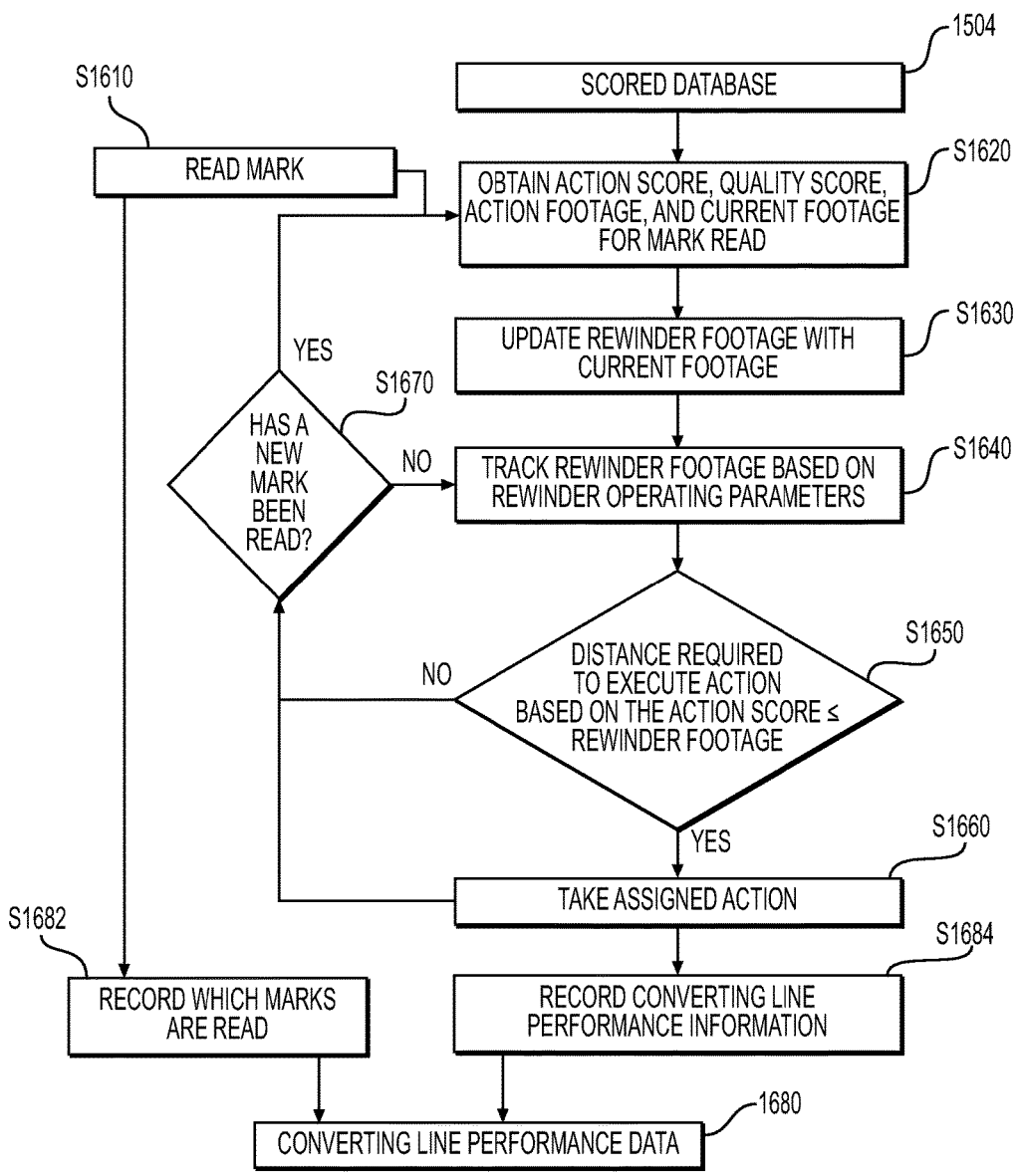
FIG. 19 is a detailed flow chart of process steps at a converting line for the embodiment shown in FIG. 16.

Steps S1360, S1370, and S1380 shown in FIG. 16 will now be described in more detail with reference to FIG. 19. A mark reading unit 1060 reads the mark 610, 620 in step S1610. The action score, quality score, action footage, and current footage is the obtained for the mark read in step S1620 from the scored database 1504. The footage of the parent roll 190 is continually being calculated as the parent roll is consumed in the converting line 1000. This is referred to as the rewinder footage and tracked in step S1640. But, the rewinder footage is updated based on the mark just read in step S1630 using the current footage obtained in step S1620. As the rewinder footage is tracked in step S1640, the distance required to execute the next action based on the action score obtained in step S1620 ("required distance") is compared to the rewinder footage in step S1650. If the rewinder footage is less than or equal to the required distance, the converting line 1000 takes the action assigned to the action score in step S1660. If the rewinder footage is greater than the required distance, the converting line 1000 then check, if a new mark has been read by the mark reading unit 1060 in step S1670. If no new mark has been read, the process returns to step S1640, but if a new mark has been read the process returns to S1620.

Additionally, performance data can be collected to improve the assignment of action scores and quality scores. In this case, the specific location marks read are recorded in step S1682. In addition, converting line performance information is recorded in step S1684. This performance information may include operating parameters of the converting line, such as speed and when any unanticipated web failures occurred on the converting line or high speed video images of the web failures. This information may also include manual override action scores. The performance information and associated location marks 620 may be recorded as converting line performance data 1680 and used to adjust the rules to assign actions, or assign fault codes and severity levels (as discussed above).

Figure 20:
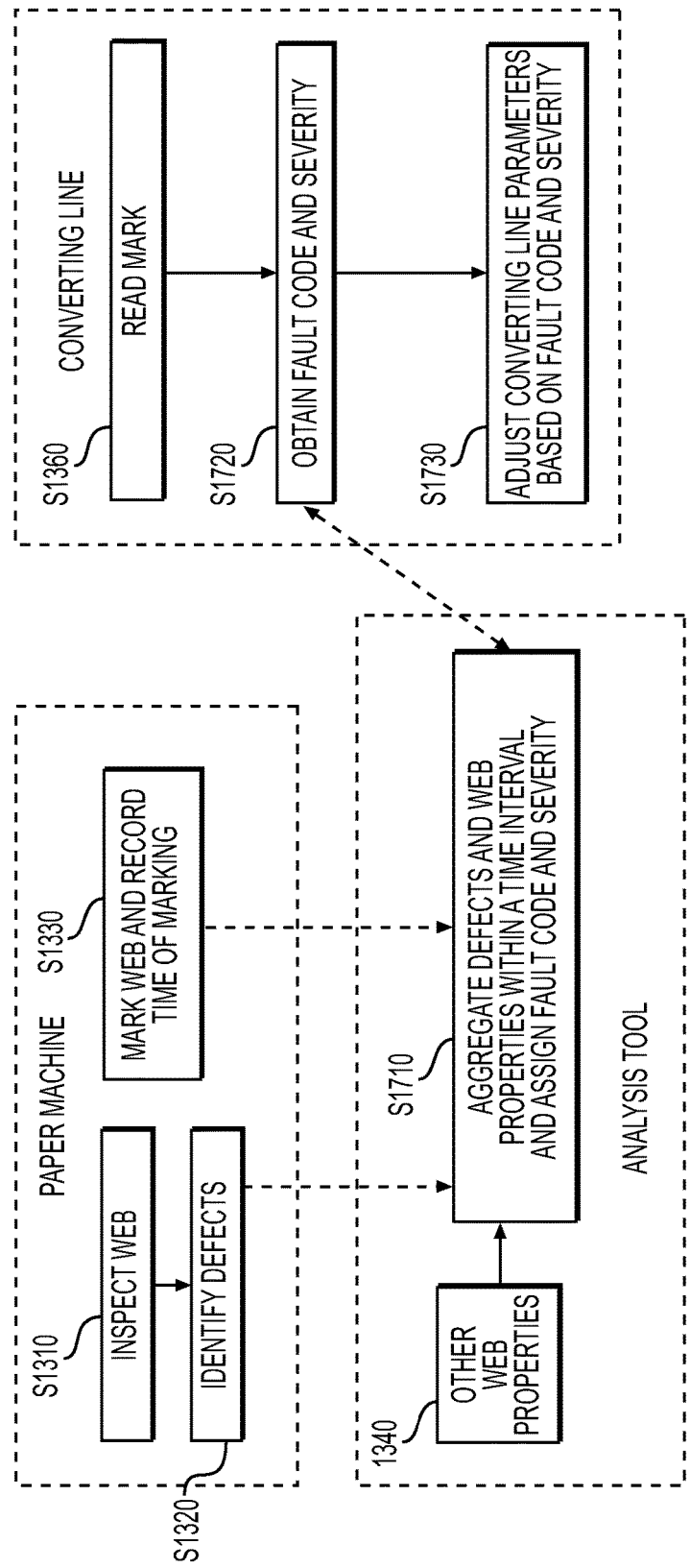
FIG. 20 is a flow chart of an alternate embodiment of our invention.
Figure 21:
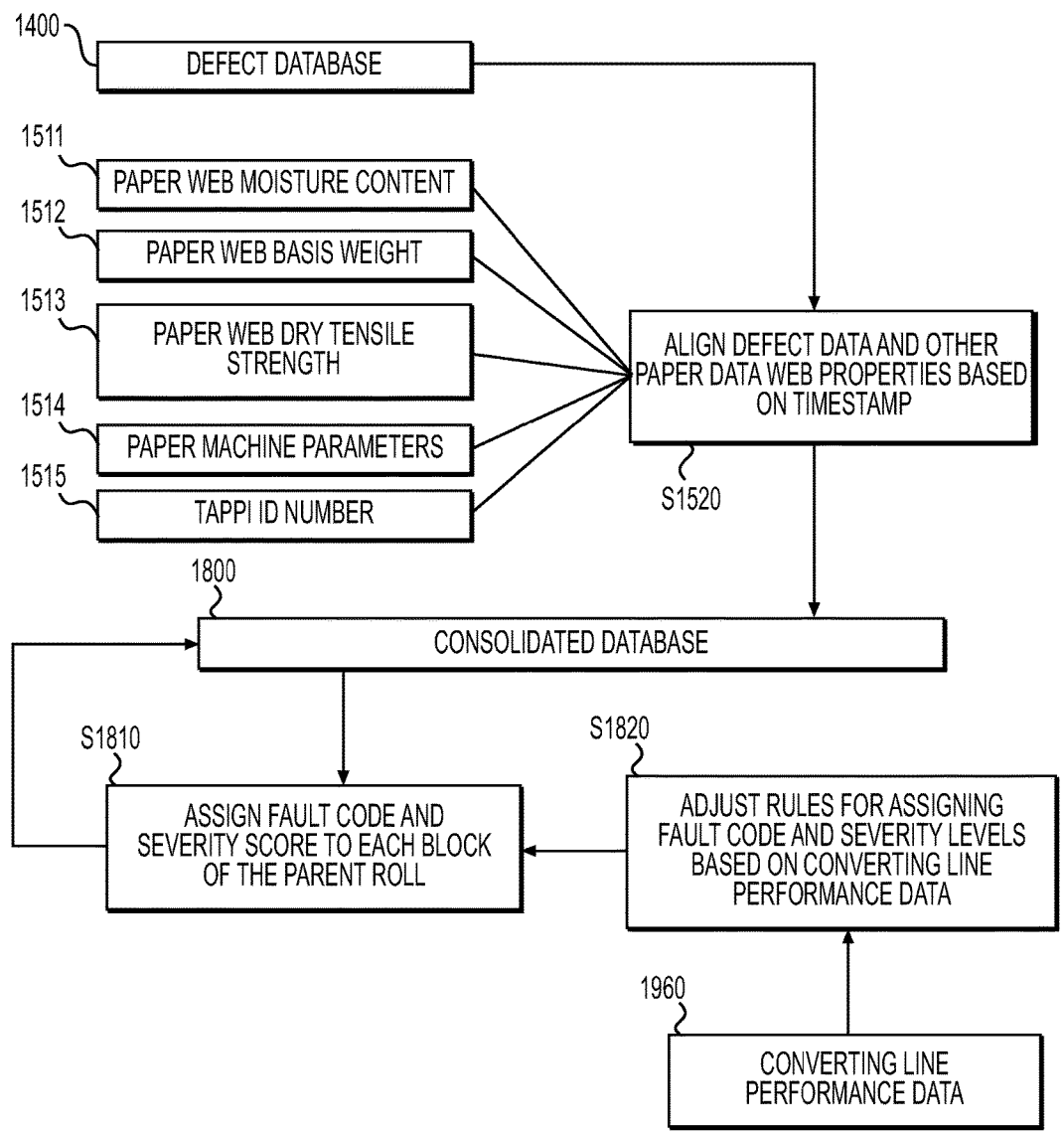
FIG. 21 is a detailed flow chart of process steps performed by an analysis tool for the embodiment shown in FIG. 20.
Figure 22:
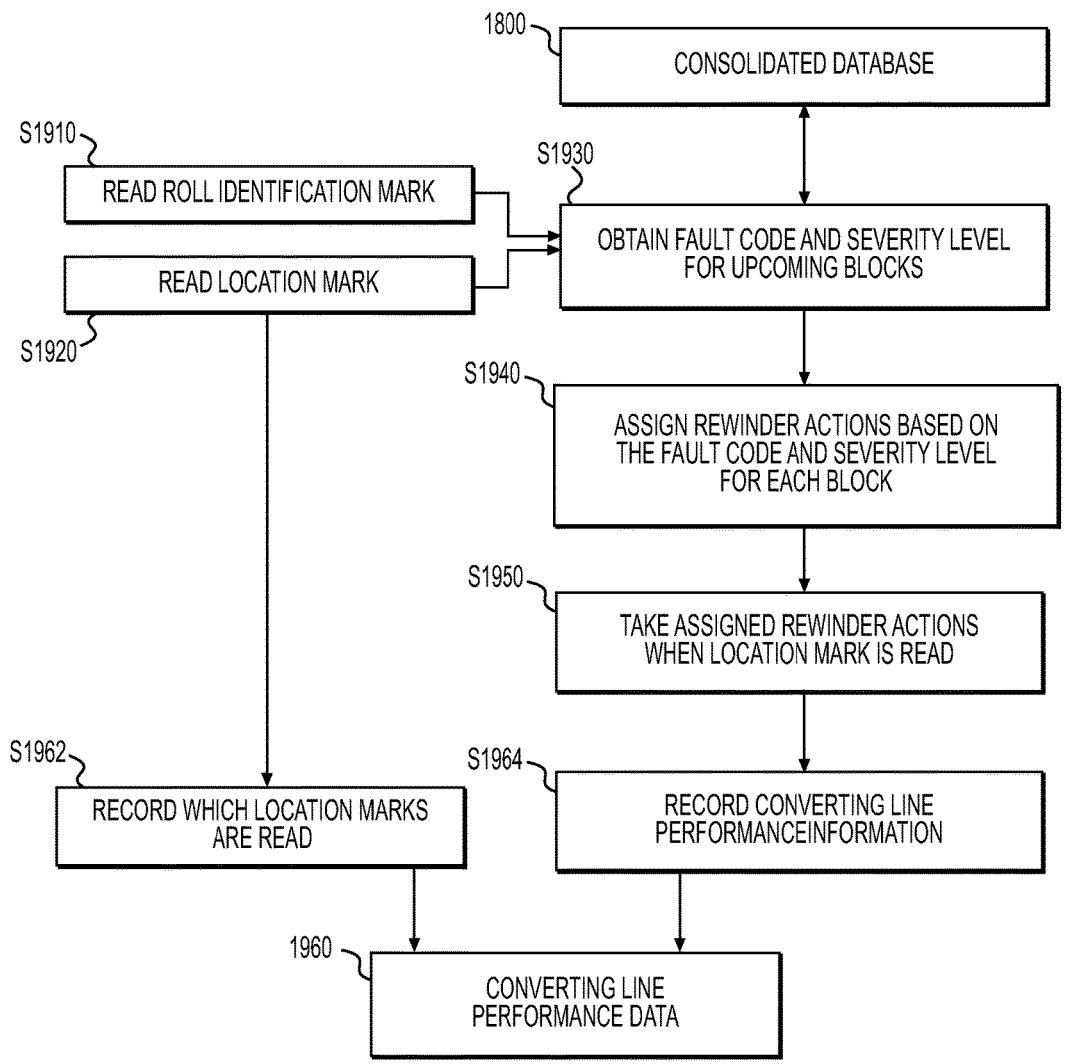
FIG. 22 is a detailed flow chart of process steps at a converting line for the embodiment shown in FIG. 20.

We will now describe an alternate preferred embodiment of our invention with reference to FIGS. 20 to 22. In this preferred embodiment, the inputs assigned and used for converting line control are the fault codes and severity levels. This embodiment is similar to the embodiment described above in reference to FIGS. 16 to 19. We will focus our discussion of this alternate embodiment to the different features of this alternate embodiment, and we will use the same reference numerals to reference the same or similar features.

FIG. 20 is a flowchart showing an overall process flow of our invention, similar to that shown in FIG. 16. In step S1710, other web properties 1340 are used to aggregate the defects identified in step S1320 over a particular time interval. The defect code and severity level are also assigned in step S1710. On the converting line, the marks read in step S1360 are used to obtain the fault codes and severity, in step S1720. In step S1720, the converting line parameters, such as converting line speed, are adjusted based upon the inputs obtained in step S1730.

Step S1710 shown in FIG. 20 will now be described in more detail with reference to FIG. 21. Step S1520 is similar to that described above in reference to FIG. 18. Here, however, the defects and web properties are aggregated and aligned into consolidated database 1800. The consolidated database 1800 is then analyzed in step S1810 according to a predetermined set of rules to assign inputs for converting line control to each block 712 (FIG. 7) of the parent roll in the consolidated database 1800. The predetermined set of rules may include those rules discussed above in conjunction with the process to assign fault codes and severity levels. These rules may be adjusted periodically in step S1550 based upon performance data 1960 from the converting line 1000.

Steps S1360, S1720, and S1730 shown in FIG. 20 will now be described in more detail with reference to FIG. 22. A mark reading unit 1060 reads both a roll identification mark 610 in step S1910 and a location mark 620 in step S1920. In the single mark embodiment, only one mark is read in step S1910. In step S1930, the fault code and severity levels for upcoming blocks 712 are obtained from the consolidated database 1800. Then, converting line actions are assigned in step S1940 to each of the upcoming blocks 712 according to a predetermined set of rules for that particular converting line 100. Steps S1910 through S1940 are repeated as successive marks are read on the paper web 102, 103. As each location mark is read, the actions to adjust converting line parameters that are associated with that mark are taken, in step S1950. As discussed above, the actions taken in step S1950 may be the actions assigned to a block 712 a predetermined number of blocks from the mark read by the reading unit 1060.

Performance data can also be collected in this embodiment to improve the assignment of fault codes and actions taken by the converting line 1000. In this case, the specific location marks read are recorded in step S1961. In addition, converting line performance information is recorded in step S1962. This performance information may include operating parameters of the converting line, such as speed and when any unanticipated web failures occurred on the converting line or high speed video images of the web failures. The performance information and associated location marks 620 may be recorded as converting line performance data 1960 and used to adjust the rules to assign actions or assign fault codes and severity levels (as discussed above).

Although this invention has been described in certain specific exemplary embodiments, many additional modifications and variations would be apparent to those skilled in the art in light of this disclosure. It is, therefore, to be understood that this invention may be practiced otherwise than as specifically described. Thus, the exemplary embodiments of the invention should be considered in all respects to be illustrative and not restrictive, and the scope of the invention to be determined by any claims supportable by this application and the equivalents thereof, rather than by the foregoing description.

INDUSTRIAL APPLICABILITY

The invention can be used to produce desirable paper products, such as paper towels and bath tissue. Thus, the invention is applicable to the paper products industry.

We claim:

1. A system for producing a paper product, the system comprising:
    (A) a paper machine for forming a paper web, the paper web including a plurality of sections in a sequence, the paper machine including:
        (a) a web analysis unit to perform at least one of inspecting the paper web and identifying properties in the paper web;
        (b) a marking unit to mark the paper web with a plurality of marks, at least one mark being assigned to each of the plurality of sections; and
        (c) a winder to wind the paper web into a parent roll, the winder being positioned after the web analysis unit and the marking unit;
    (B) an analysis tool configured to assign an action score to each section of the paper web based upon the identified properties in that section of the paper web, at least one action score having an action value, the action value being a value of the action score that indicates an actionable risk of converting line failure; and
    (C) a converting line for converting the paper web into a paper product, the converting line having a plurality of operating parameters and including:
        (a) an unwind stand to unwind the paper web from the parent roll;
        (b) a mark reading unit that (i) reads at least one of the plurality of marks on the paper web and (ii) produces a corresponding output from the mark that has been read;
        (c) a controller that receives the output from the mark reading unit and is configured:
            (i) to obtain the action score associated with a second one of the plurality of marks, the second one of the plurality of marks being the next mark with an action value after the at least one mark read by the reading unit,
            (ii) to calculate a distance between the at least one mark read by the reading unit and the second one of the plurality of marks, and
            (iii) to change at least one operational parameter of the converting line based upon the action score of the second one of the plurality of marks when the calculated distance is less than a threshold; and
        (d) a finisher, the paper web being fed to the finisher and converted into a paper product.

2. The system of claim 1, wherein the paper web is unwound from the parent roll at a parent roll speed, and the controller changes the parent roll speed as the at least one operational parameter.

3. The system of claim 1, wherein the controller stops the paper web from being unwound as the at least one operational parameter.

4. The system of claim 1, further comprising a second paper web being unwound from a second parent roll, the unwind stand holding both the paper web and the second paper web and the controller switching between (i) feeding the paper web to the finisher and (ii) feeding the second paper web to the finisher, as the at least one operational parameter.

5. The system of claim 4, wherein the unwind stand has a flying splice to switch from feeding one of the paper web and the second paper web to the finisher, the controller splicing between the paper web and the second paper web, as the at least one operational parameter.

6. The system of claim 1, wherein controller is further configured to calculate the threshold based on a distance required to change the at least one operational parameter.

7. The system of claim 1, wherein the action score is based on an inter-relationship of the web properties in one of the plurality of sections of the paper web.

8. The system of claim 7, wherein the value of the action score is based on a likelihood that the inter-relationship of the web properties will result in converting line failure.

9. The system of claim 1, wherein the web properties include web defects.

10. The system of claim 9, wherein the web defects include at least one of a hole, a tear, a wrinkle, a web break, and a chemical coating streak.

11. The system of claim 1, wherein the web properties include at least one of moisture content, basis weight, and tensile strength.

12. The system of claim 1, wherein the reading unit includes a light source to illuminate a portion of the paper web having the at least one of the plurality of marks and a camera to visually identify the at least one of the plurality of marks.

13. The system of claim 12, wherein the light source is an ultraviolet light source.

14. The system of claim 1, wherein the mark reading unit reads the at least one of the plurality of marks on the paper web as the paper web is being unwound from the parent roll.

15. The system of claim 14, wherein the mark reading unit is positioned downstream from the unwind stand and prior to the finisher.

16. The system of claim 14, wherein the mark reading unit is positioned at a bowed roll.

17. The system of claim 1, further comprising a plurality of web analysis units.

18. The system of claim 1, wherein the web analysis unit comprises a camera and a light source for inspecting the paper web.

19. The system of claim 18, wherein the web analysis unit inspects for web defects.

20. The system of claim 19, wherein the web defects include at least one of a hole, a tear, a wrinkle, a web break, and a chemical coating streak.

21. The system of claim 1, wherein the web analysis unit comprises a web property scanner for identifying properties in the web.

22. The system of claim 21, wherein the web properties include at least one of moisture content and basis weight.

23. The system of claim 1, wherein the marking unit applies ink to the paper web.

24. The system of claim 23, wherein the applied ink is visible under ultraviolet light.

25. The system of claim 1, wherein the finisher includes a rewinder.

26. The system of claim 1, wherein the finisher includes a folder.

27. The system of claim 1, wherein the action score is one of the web properties in one of the plurality of sections of the paper web.

28. The system of claim 27, wherein the value of the action score is based on a likelihood that the web properties will result in converting line failure.

29. The system of claim 28, wherein the web properties include web defects.

30. The system of claim 29, wherein the web defects include at least one of a hole, a tear, a wrinkle, a web break, and a chemical coating streak.

31. The system of claim 28, wherein the web properties include at least one of moisture content, basis weight, and tensile strength.

32. A system for producing a paper product, the system comprising:
(A) a paper machine for forming a paper web, the paper web including a plurality of sections, the paper machine including:
  (a) a web analysis unit to perform at least one of inspecting the paper web and identifying properties in the paper web;
  (b) a marking unit to mark the paper web with a plurality of marks, at least one mark being assigned to each of the plurality of sections; and
  (c) a winder to wind the paper web into a parent roll, the winder being positioned after the web analysis unit and the marking unit;
(B) an analysis tool configured to assign a quality score to each section of the paper web based upon the identified properties in that section of the paper web, at least one quality score having an action value, the action value being a value of the quality score that indicates an unacceptable quality defect; and
(C) a converting line for converting the paper web into a paper product, the converting line having a plurality of operating parameters and including:
  (a) an unwind stand to unwind the paper web from the parent roll;
  (b) a mark reading unit that (i) reads at least one of the plurality of marks on the paper web and (ii) produces a corresponding output from the mark that has been read;
  (c) a finisher, the paper web being fed to the finisher and converted into a paper product; and
  (d) a controller that receives the output from the mark reading unit and is configured:
    (i) to obtain the quality score associated with the at least one mark read by the reading unit, and
    (ii) to cause the finisher to reject the paper product corresponding to one of the plurality of paper web sections when the quality score of the at least one mark read by the reading unit has an action value.

33. The system of claim 32, wherein the quality score is based on an inter-relationship of the web properties in one of the plurality of sections of the paper web.

34. The system of claim 33, wherein an action value is assigned as the quality score when inter-relationship of the web properties results in an unacceptable quality defect.

35. The system of claim 32, wherein the web properties include web defects.

36. The system of claim 35, wherein the web defects include at least one of a hole, a tear, a wrinkle, a web break, and a chemical coating streak.

37. The system of claim 32, wherein the web properties include at least one of moisture content, basis weight, and tensile strength.

38. The system of claim 32, wherein the reading unit includes a light source to illuminate a portion of the paper web having the at least one of the plurality of marks and a camera to visually identify the at least one of the plurality of marks.

39. The system of claim 38, wherein the light source is an ultraviolet light source.

40. The system of claim 32, wherein the mark reading unit reads the at least one of the plurality of marks on the paper web as the paper web is being unwound from the parent roll.

41. The system of claim 40, wherein the mark reading unit is positioned downstream from the unwind stand and prior to the finisher.

42. The system of claim 41, wherein the mark reading unit is positioned at a bowed roll.

43. The system of claim 32, further comprising a plurality of web analysis units.

44. The system of claim 32, wherein the web analysis unit comprises a camera and a light source for inspecting the paper web.

45. The system of claim 44, wherein the web analysis unit inspects for web defects.

46. The system of claim 45, wherein the web defects include at least one of a hole, a tear, a wrinkle, a web break, and a chemical coating streak.

47. The system of claim 32, wherein the web analysis unit comprises a web property scanner for identifying properties in the web.

48. The system of claim 47, wherein the web properties include at least one of moisture content and basis weight.

49. The system of claim 32, wherein the marking unit applies ink to the paper web.

50. The system of claim 49, wherein the applied ink is visible under ultraviolet light.

51. The system of claim 32, wherein the finisher includes a rewinder and the paper product rejected is a log of paper.

52. The system of claim 32, wherein the finisher includes a folder and the paper product rejected is a stack of folded paper product.

53. The system of claim 32, wherein the quality score is based on the web properties in one of the plurality of sections of the paper web.

54. The system of claim 53, wherein the web properties include web defects.

55. The system of claim 54, wherein an action value is assigned as the quality score when at least one web defect in the one of the plurality of sections of the paper web is an unacceptable quality defect.

56. The system of claim 54, wherein the web defects include at least one of a hole, a tear, a wrinkle, a web break, and a chemical coating streak.

57. The system of claim 53, wherein the web properties include at least one of moisture content, basis weight, and tensile strength.

58. The system of claim 57, wherein an action value is assigned as the quality score when at least one web property in the one of the plurality of sections of the paper web is an unacceptable quality defect.

* * * * *